(12) United States Patent
Mottola et al.

(10) Patent No.: US 10,863,998 B2
(45) Date of Patent: Dec. 15, 2020

(54) MEDICAL GRASPING DEVICE

(71) Applicant: Merit Medical Systems, Inc., South Jordan, UT (US)

(72) Inventors: Jim Mottola, West Jordan, UT (US); Peter Sutcliff, Palm Coast, FL (US); F. Mark Ferguson, Salt Lake City, UT (US); Ken Sykes, Bluffdale, UT (US); Gregory R. McArthur, Sandy, UT (US); Nate Shirley, Pleasant Grove, UT (US); Richard P. Jenkins, Bluffdale, UT (US); Christopher Cindrich, Draper, UT (US); Denise Hallisey, Wethersfield, CT (US)

(73) Assignee: Merit Medical Systems, Inc., South Jordan, UT (US)

( * ) Notice: Subject to any disclaimer, the term of this patent is extended or adjusted under 35 U.S.C. 154(b) by 532 days.

(21) Appl. No.: 15/608,359

(22) Filed: May 30, 2017

(65) Prior Publication Data

US 2017/0348013 A1  Dec. 7, 2017

Related U.S. Application Data

(60) Provisional application No. 62/344,579, filed on Jun. 2, 2016.

(51) Int. Cl.
*A61F 17/00* (2006.01)
*A61B 17/22* (2006.01)
(Continued)

(52) U.S. Cl.
CPC .............. *A61B 17/22* (2013.01); *A61B 10/02* (2013.01); *A61B 17/22031* (2013.01); *A61B 2017/2215* (2013.01); *A61B 2017/22035* (2013.01); *A61B 2017/305* (2013.01); *A61F 2/011* (2020.05); *A61F 2/95* (2013.01); *A61F 2002/016* (2013.01); *A61F 2002/9528* (2013.01)

(58) Field of Classification Search
CPC ... A61B 17/22; A61B 17/22031; A61B 10/02; A61B 2017/22035; A61B 2017/2215; A61B 2017/305
See application file for complete search history.

(56) References Cited

U.S. PATENT DOCUMENTS 1,443,086 A * 1/1923 Muchow ................ A61B 17/30
                                                            294/99.2
3,958,576 A   5/1976 Komiya
(Continued)

FOREIGN PATENT DOCUMENTS

EP         3097871      11/2016
WO      2016089865      6/2019

OTHER PUBLICATIONS

International Search Report and Written Opinion dated Aug. 29, 2017 for PCT/US2017/034998.
European Search Report dated Dec. 10, 2019 for EP17807330.0.

*Primary Examiner* — Julie A Szpira
(74) *Attorney, Agent, or Firm* — Stoel Rives LLP

(57) ABSTRACT

A medical grasping device is disclosed. The medical grasping device may be configured to retrieve an object from within a body lumen. A medical grasping device assembly, wherein a portion of the medical grasping device is disposed within a lumen of a delivery sheath, and methods of using the medical grasping device assembly are also disclosed.

16 Claims, 15 Drawing Sheets

(51) Int. Cl.
*A61B 10/02* (2006.01)
*A61B 17/221* (2006.01)
*A61F 2/01* (2006.01)
*A61B 17/30* (2006.01)
*A61F 2/95* (2013.01)

(56) References Cited

U.S. PATENT DOCUMENTS

| | | | |
|---|---|---|---|
| 4,844,065 A * | 7/1989 | Faulkner | A61B 17/30 606/107 |
| 6,361,540 B1 * | 3/2002 | Gauderer | A61B 17/221 606/106 |
| D689,606 S | 9/2013 | John et al. | |
| 8,529,583 B1 | 9/2013 | Golden et al. | |
| D710,006 S | 7/2014 | John et al. | |
| D725,265 S | 3/2015 | John et al. | |
| D758,581 S | 6/2016 | Michelini et al. | |
| D779,668 S | 2/2017 | Michelini et al. | |
| 2002/0143387 A1 | 10/2002 | Soetikno et al. | |
| 2002/0151762 A1 * | 10/2002 | Rocheleau | A61B 17/0401 600/30 |
| 2007/0135813 A1 * | 6/2007 | Yamamoto | A61B 18/1445 606/46 |
| 2007/0186933 A1 | 8/2007 | Domingo et al. | |
| 2008/0269774 A1 | 10/2008 | Garcia et al. | |
| 2013/0231686 A1 | 9/2013 | Durgin et al. | |
| 2014/0058425 A1 * | 2/2014 | Porat | A61B 17/2812 606/167 |
| 2014/0135820 A1 * | 5/2014 | Schaller | A61B 17/30 606/205 |
| 2014/0142609 A1 | 5/2014 | Keegan et al. | |
| 2015/0327910 A1 * | 11/2015 | Brooke | A61B 17/30 606/52 |
| 2015/0359669 A1 * | 12/2015 | Grueebler | A61F 9/00736 606/205 |

* cited by examiner

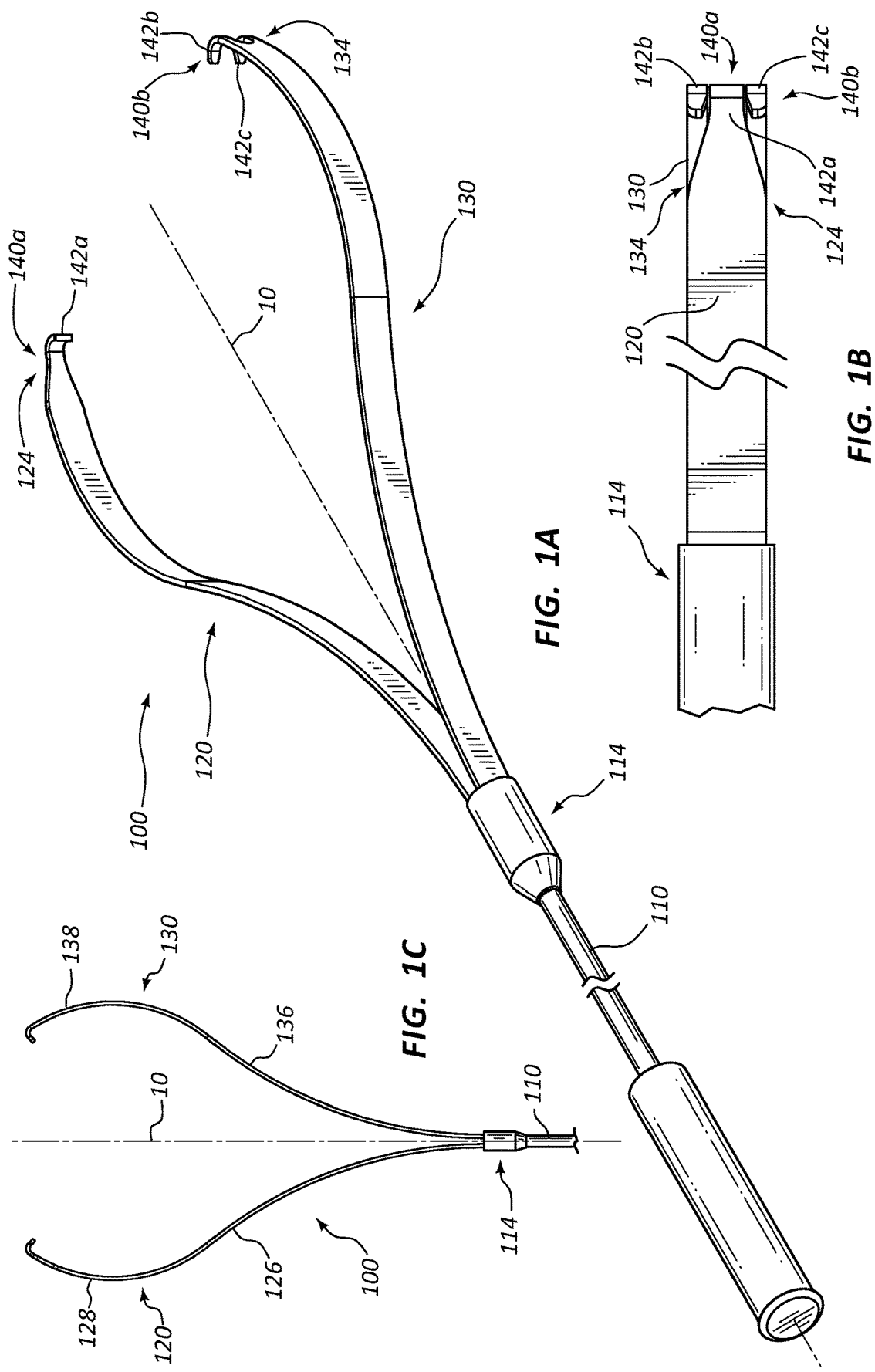

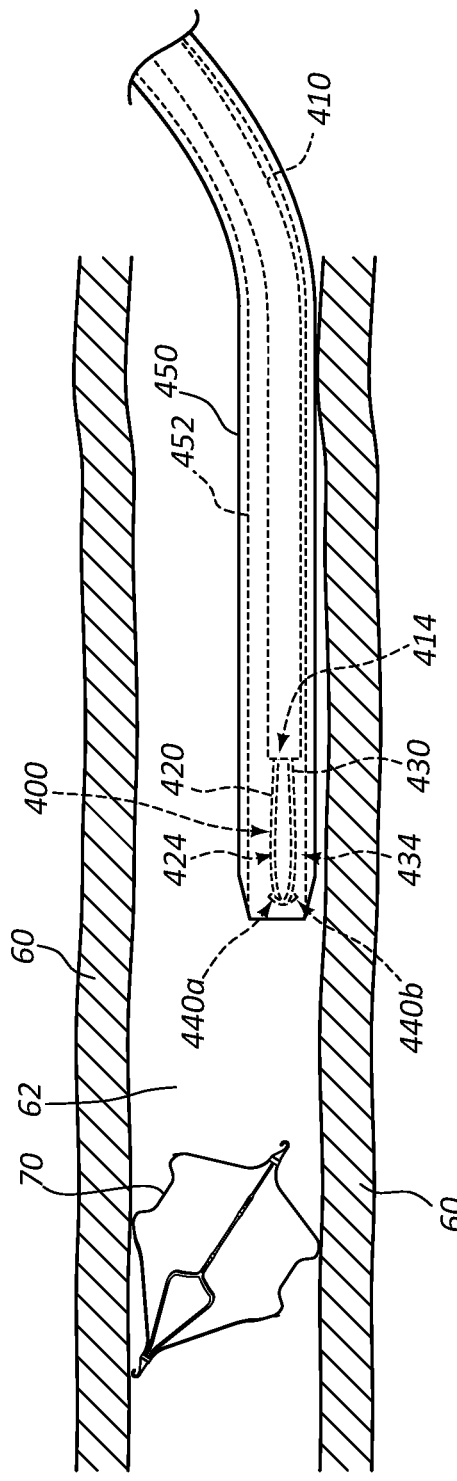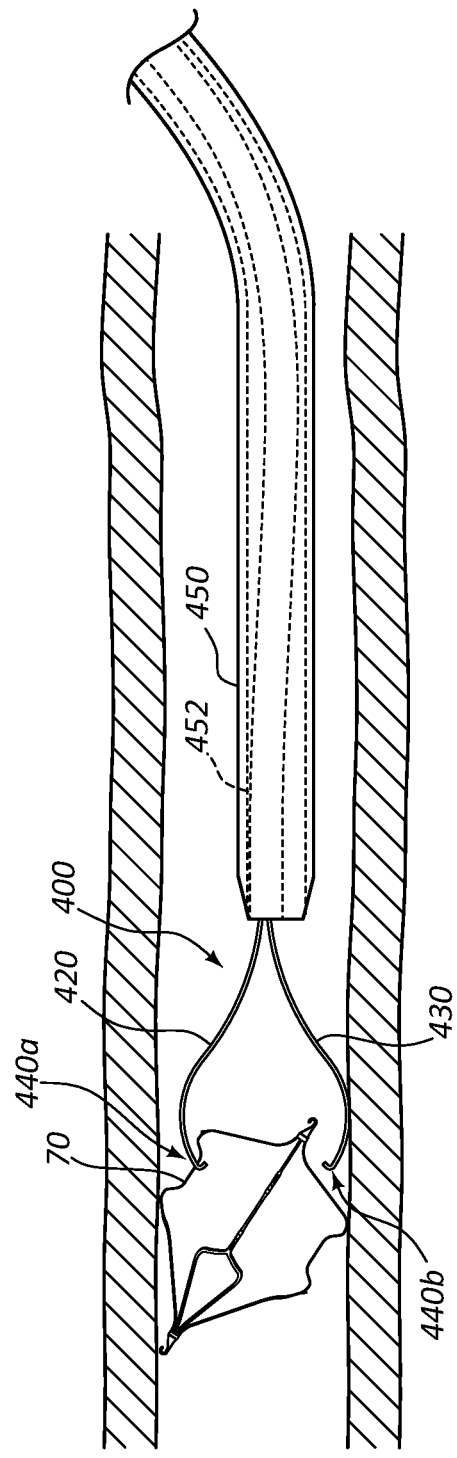

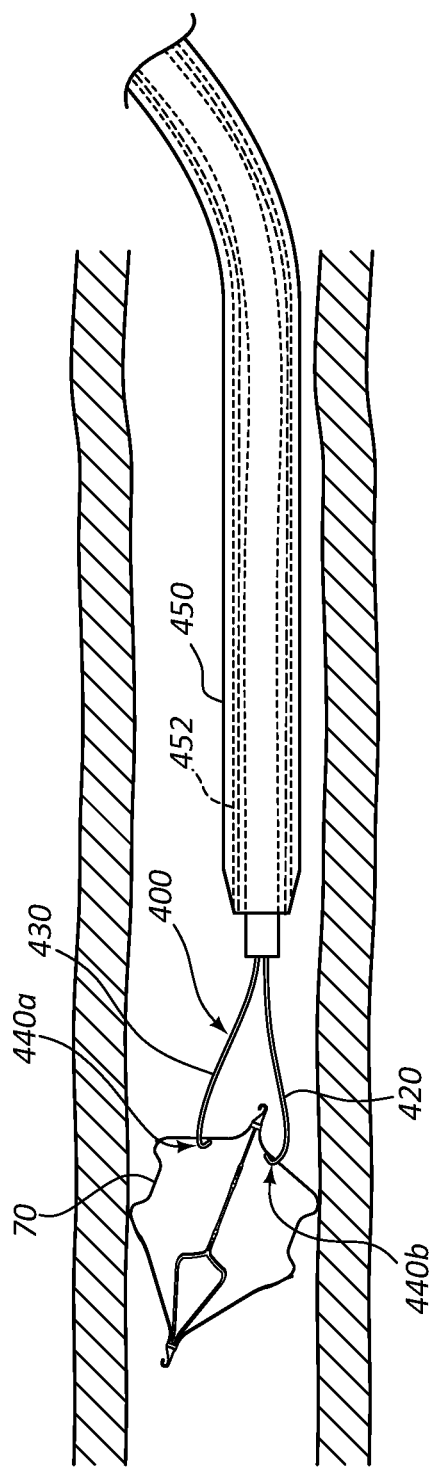
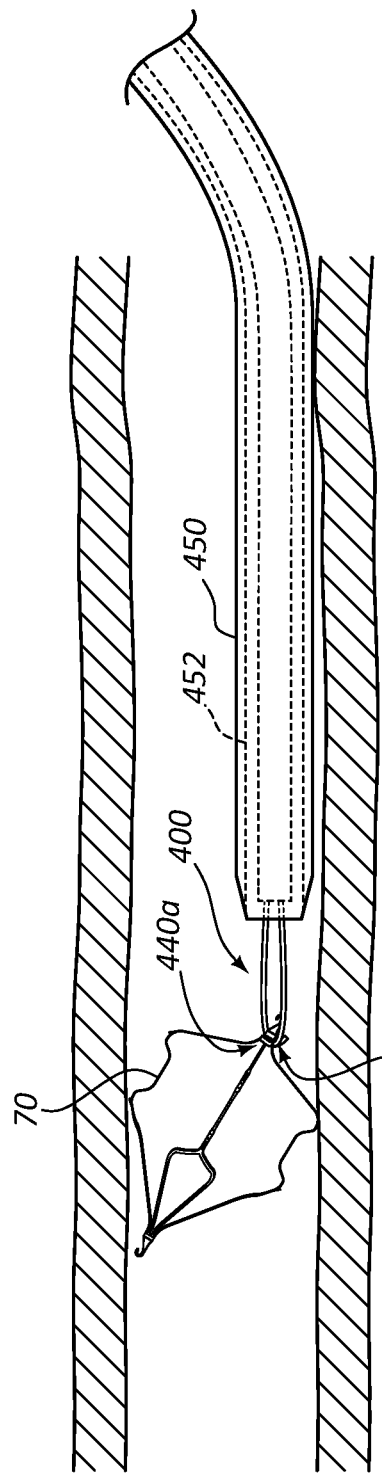
FIG. 4C
FIG. 4D

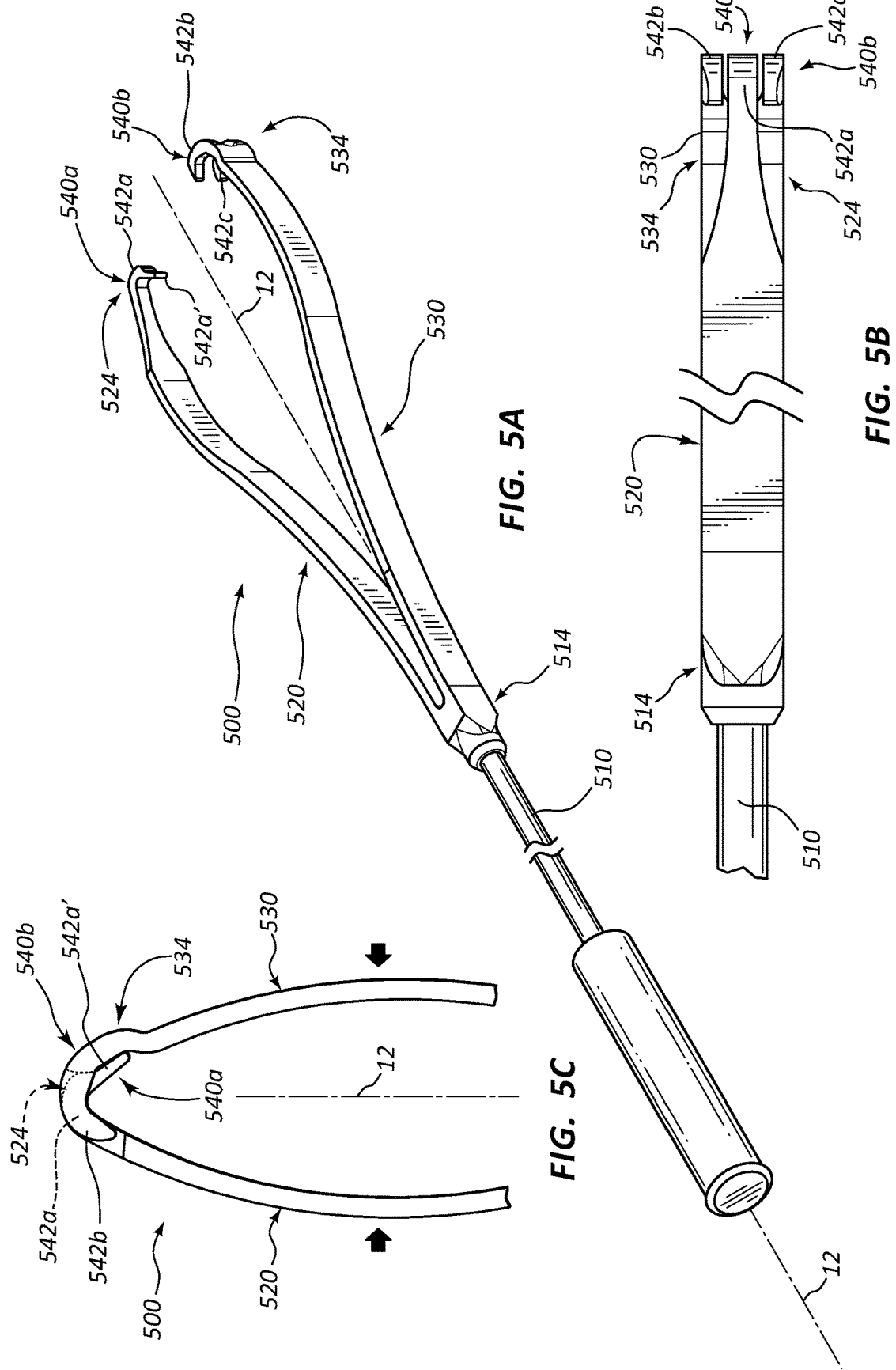

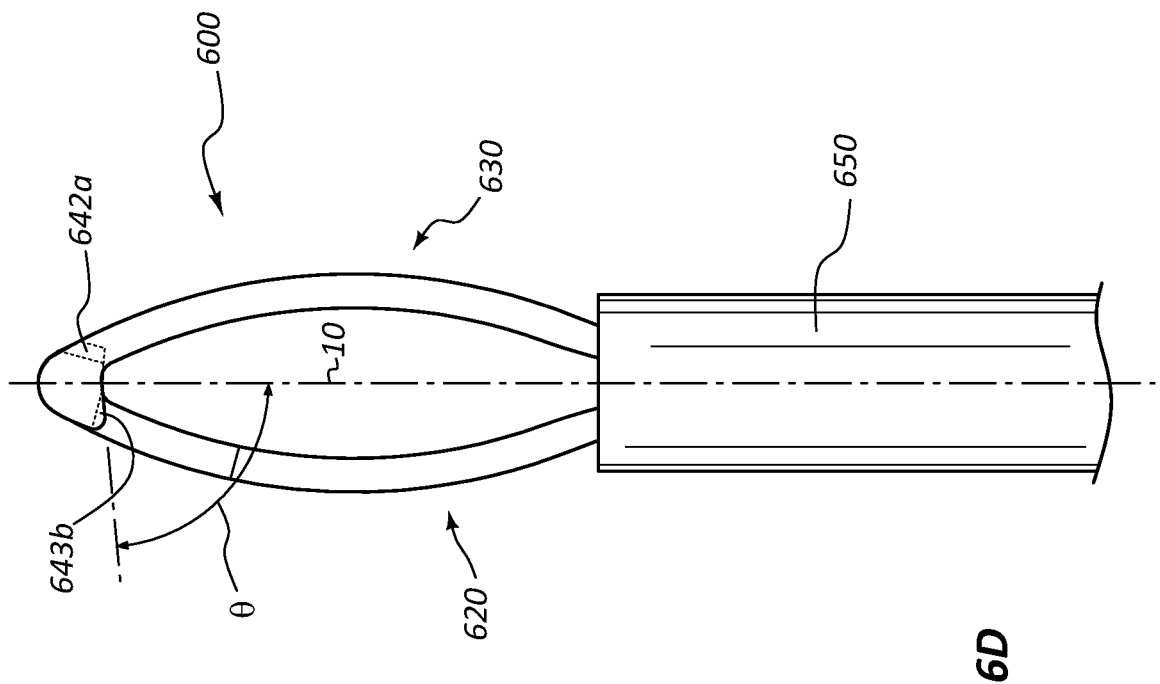
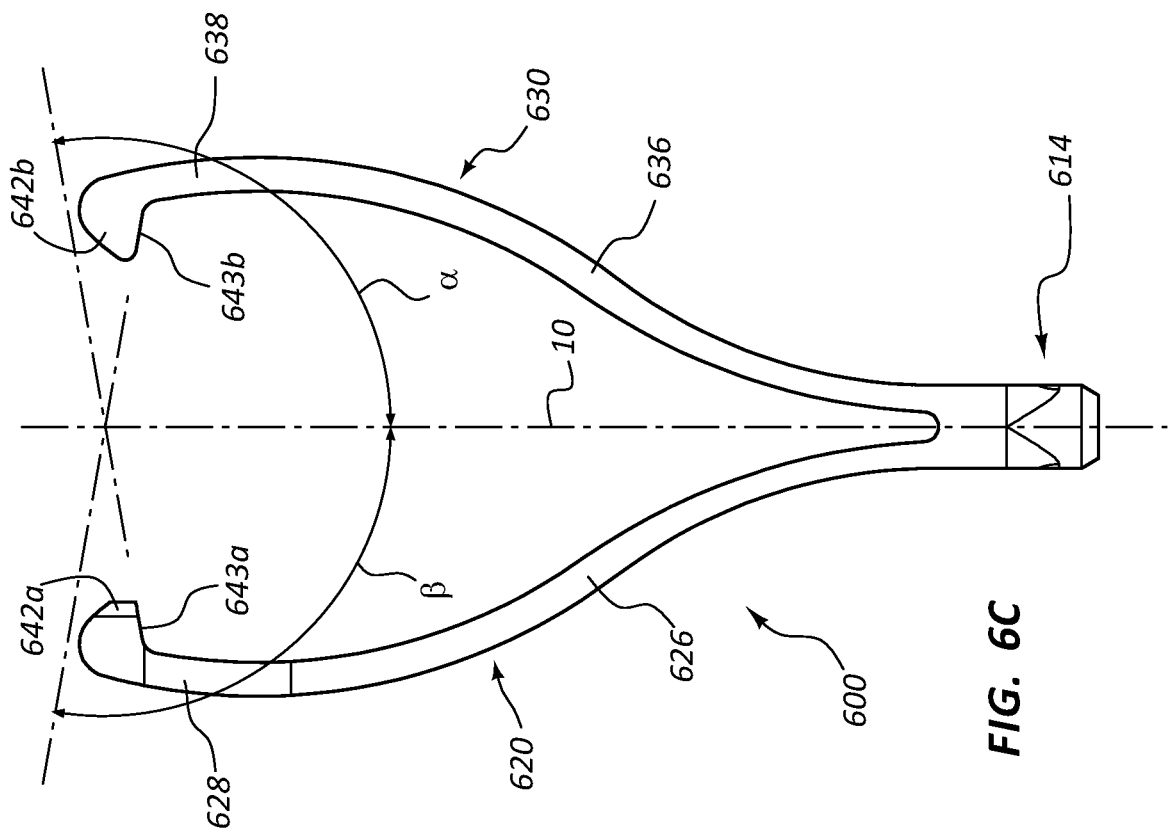
FIG. 6C
FIG. 6D

MEDICAL GRASPING DEVICE

RELATED APPLICATIONS

This application claims priority to U.S. Provisional Application No. 62/344,579, filed on Jun. 2, 2016 and titled, "Medical Grasping Device," which is hereby incorporated by reference in its entirety.

TECHNICAL FIELD

The present disclosure relates generally to medical grasping devices. More specifically, the present disclosure relates to medical grasping devices configured for retrieval of objects from body lumens and methods of use.

BRIEF DESCRIPTION OF THE DRAWINGS

The embodiments disclosed herein will become more fully apparent from the following description and appended claims, taken in conjunction with the accompanying drawings. While various aspects of the embodiments are presented in drawings, the drawings depict only typical embodiments, which will be described with additional specificity and detail through use of the accompanying drawings in which:

FIG. 1A is a perspective view of an embodiment of a medical grasping device.

FIG. 1B is a side view of a portion of the medical grasping device of FIG. 1A.

FIG. 1C is a front view of a portion of the medical grasping device of FIG. 1A.

FIG. 4A is a side view of an embodiment of a medical grasping device assembly disposed in a body lumen.

FIG. 4B is a side view of the medical grasping device assembly of FIG. 4A wherein resilient prongs of the medical grasping device are partially distally displaced from within a lumen of a delivery sheath.

FIG. 4C is a side view of the medical grasping device assembly of FIG. 4A wherein the resilient prongs of the medical grasping device are fully distally displaced from within the lumen of the delivery sheath.

FIG. 4D is a side view of the medical grasping device assembly of FIG. 4A wherein the medical grasping device has secured a vascular filter.

FIG. 5A is a perspective view of another embodiment of a medical grasping device in an open configuration.

FIG. 5B is a side view of a portion of the medical grasping device of FIG. 5A.

FIG. 5C is a front view of a portion of the medical grasping device of FIG. 5A in a closed configuration.

FIG. 6C is a front view of the medical grasping device of FIG. 6A in an open configuration.

FIG. 6D is a front view of the medical grasping device of FIG. 6A in a closed configuration.

DETAILED DESCRIPTION

Figure 2A:
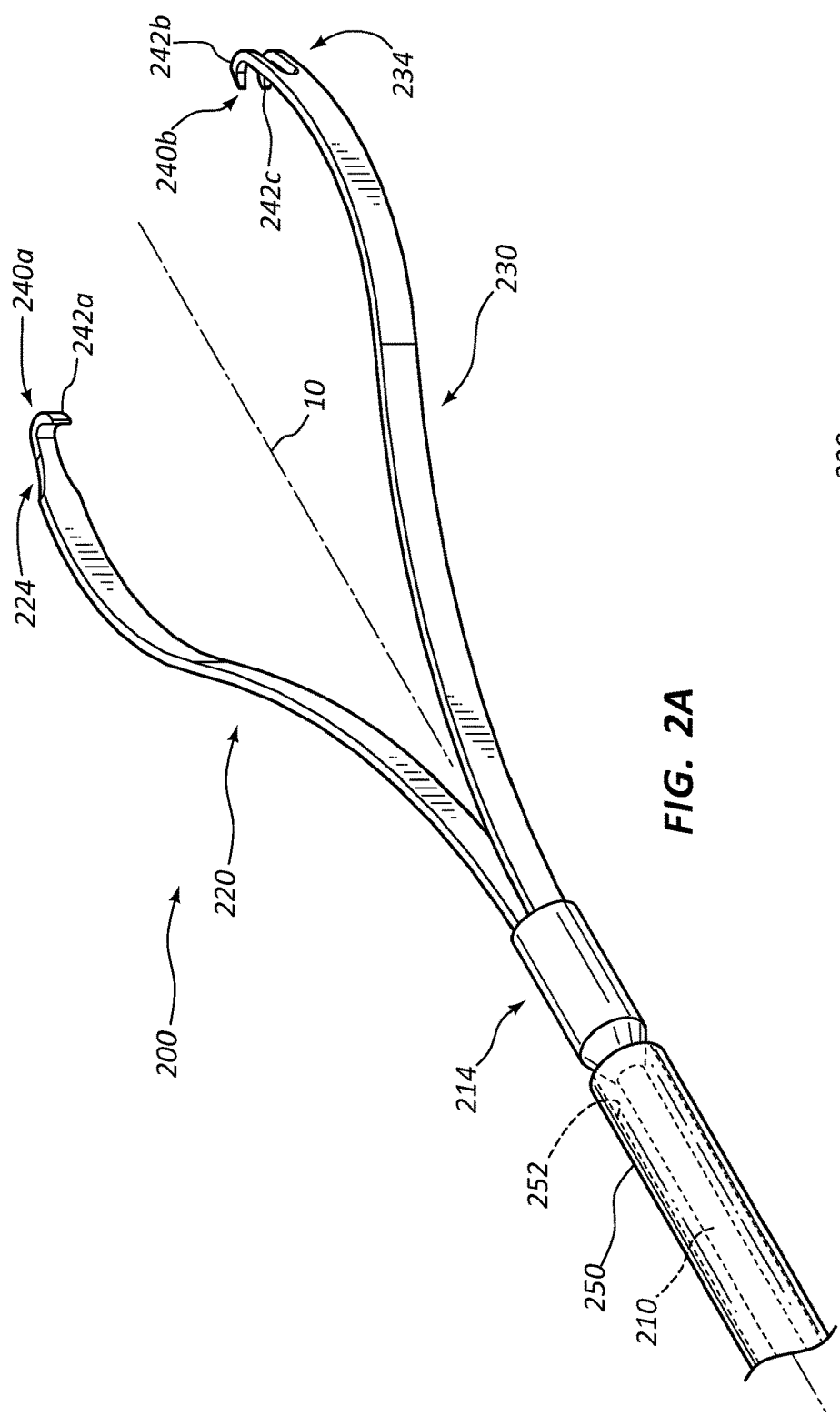
FIG. 2A is a perspective view of another embodiment of a medical grasping device.

The various embodiments disclosed herein generally relate to medical grasping devices. More specifically, the various embodiments relate to medical grasping device systems, for example, medical grasping device assemblies and related methods. In some embodiments, the medical grasping device assembly comprises an elongate member, a plurality of resilient prongs, and a delivery sheath. Also disclosed herein are methods of utilizing a medical grasping device assembly.

It will be appreciated that various features are sometimes grouped together in a single embodiment, figure, or description thereof for the purpose of streamlining the disclosure. Many of these features may be used alone and/or in combination with one another.

Embodiments may be understood by reference to the drawings, wherein like parts are designated by like numerals throughout. It will be readily understood that the components of the present disclosure, as generally described and illustrated in the drawings herein, could be arranged and designed in a wide variety of different configurations. Thus, the following more detailed description of the embodiments of the apparatus is not intended to limit the scope of the disclosure, but is merely representative of possible embodiments of the disclosure. In some cases, well-known structures, materials, or operations are not shown or described in detail. While the various aspects of the embodiments are presented in drawings, the drawings are not necessarily drawn to scale unless specifically indicated.

The phrases "connected to," "coupled to," and "in communication with" refer to any form of interaction between two or more entities, including but not limited to mechanical, electrical, magnetic, electromagnetic, fluid, and thermal interaction. Two components may be coupled to each other even though they are not in direct contact with each other. For example, two components may be coupled to each other through an intermediate component.

The terms "proximal" and "distal" refer to opposite ends of a medical device, including the devices disclosed herein. As used herein, the proximal portion of a medical device is the portion nearest a practitioner during use, while the distal portion is a portion at the opposite end. For example, the proximal end of a medical grasping device is defined as the end closest to the practitioner during insertion or utilization of the medical grasping device. The distal end is the end opposite the proximal end, along the longitudinal direction of the medical grasping device.

The terms "foreign body" and "foreign object" refer to any item, matter, or substance, such as a medical device or an embolism, which may be disposed or positioned within a body lumen. In some embodiments, the foreign body or object may be undesirable or unwanted. Specifically, a foreign body or object may be an item that a practitioner desires or targets to remove or retrieve from within a body lumen. For example, the foreign body or object may comprise a medical device (e.g., a vascular filter or a stent) that is disposed within a vessel, and a medical grasping device of the present disclosure may be configured to retrieve the medical device from within the vessel. Further, disclosure herein relating to displacement of foreign objects may analogously be applied to any target for displacement or removal, including, for example, bodily structures or materials.

The term "resilient" refers to a component, device, or object that is formed with a particular shape, that can then be elastically deformed into a different shape, but that can return to the original shape when unconstrained. For example, a resilient prong may be formed with a first shape, the resilient prong may then be constrained (i.e., disposed within a lumen of a sheath) to elastically deform it into a second shape, then unconstrained (i.e., displaced out of the lumen of the sheath) such that the resilient prong returns to its first shape. Shape memory alloys, including NITINOL, are examples of resilient materials.

FIG. 1A illustrates an embodiment of a medical grasping device 100. As depicted, the medical grasping device 100 can comprise an elongate member 110. The medical grasping device 100 may also comprise at least two resilient prongs 120, 130. In the illustrated embodiment, the medical grasping device 100 comprises a first resilient prong 120 and a second resilient prong 130. In other embodiments, the medical grasping device 100 may comprise three resilient prongs, four resilient prongs, or more resilient prongs. The first and second resilient prongs 120, 130 are coupled to the elongate member 110 at a distal end 114 of the elongate member 110, and each of the first and second resilient prongs 120, 130 can extend distally from the distal end 114 of the elongate member 110.

At least one engagement feature 140*a* may be disposed at a distal end 124 of the first resilient prong 120. Likewise, at least one engagement feature 140*b* may be disposed at a distal end 134 of the second resilient prong 130. In the illustrated embodiment, the engagement feature 140*a* comprises one curved portion 142*a*, wherein the curved portion 142*a* is disposed at the distal end 124 of the first resilient prong 120. Also, as illustrated, the engagement feature 140*b* comprises two curved portions 142*b*, 142*c*, wherein the two curved portions 142*b*, 142*c* are disposed at the distal end 134 of the second resilient prong 130. The one curved portion 142*a* of the first resilient prong 120 may be configured to interlock or engage with the two curved portions 142*b*, 142*c* of the second resilient prong 130 when the distal ends 124, 134 of the first and second resilient prongs 120, 130, respectively, are displaced toward each other (as discussed in further detail below). The interlocking of the curved portions 142*a*, 142*b*, 142*c* may be configured to secure a target foreign object disposed within a body lumen. For example, a target foreign object may be secured before any force is applied on the target foreign object by a medical grasping device. Such a configuration may facilitate a traumatic, or less traumatic, securement of the target foreign object prior to displacement of the target foreign object.

Other configurations of engagement features are also contemplated. For example, the engagement features may comprise one or more L-shaped portions (i.e., portions that are not substantially curved). In another example, a first engagement feature may comprise two teeth or projections separated by a gap or slot and a second engagement feature, which is configured to interlock with the first engagement feature, wherein the second engagement feature may comprise a single tooth or projection configured to be disposed, at least partially, within the gap or slot of the first engagement feature.

With continued reference to FIG. 1A, each of the first resilient prong 120 and the second resilient prong 130 curves outwardly from an extension of a longitudinal axis 10 of the elongate member 110. In contrast, each of the curved portions 142*a*, 142*b*, 142*c* curves inwardly toward the extension of the longitudinal axis 10 of the elongate member 110.

As depicted, each of the first resilient prong 120 and the second resilient prong 130 extends from the distal end 114 of the elongate member 110 such that the first resilient prong 120 extends in a substantially opposite direction from the second resilient prong 130. Stated another way, the extension of the first resilient prong 120 from the elongate member 110 generates or forms a substantially mirror image of the extension of the second resilient prong 130 from the elongate member 110, and vice versa. As illustrated, the first resilient prong 120 extends from a first portion at the distal end 114 of the elongate member 110 and the second resilient prong 130 extends from a second portion at the distal end 114 of the elongate member 110, wherein the first position and the second position are disposed at substantially opposite positions along a circumference of the distal end 114 of the elongate member 110. As such, each of the first resilient prong 120 and the second resilient prong 130 is substantially disposed within a single plane. Other dispositions of the first and second resilient prongs 120, 130 around the circumference of the distal end 114 of the elongate member are also within the scope of this disclosure.

FIG. 1B is a side view of a portion of the medical grasping device 100 of FIG. 1A. In the illustrated embodiment, the relative position of the first resilient prong 120 in relation to the position of the second resilient prong 130 is shown. As described above, at least one engagement feature 140*a* can be disposed at the distal end 124 of the first resilient prong 120. Likewise, at least one engagement feature 140*b* may be disposed at the distal end 134 of the second resilient prong 130. The engagement feature 140*a* of the first resilient prong 120, as illustrated, comprises one curved portion 142*a*, wherein the curved portion 142*a* is disposed at the distal end 124 of the first resilient prong 120. The engagement feature 140*b* of the second resilient prong 130 comprises two curved portions 142*b*, 142*c*, wherein the curved portions 142*b*, 142*c* are disposed at the distal end 134 of the second resilient prong 130. As depicted, the one curved portion 142*a* of the first resilient prong 120 is configured to interlock with or engage with the two curved portions 142*b*, 142*c* of the second resilient prong 130. For example, when the distal ends 124, 134 of the first and second resilient prongs 120, 130, respectively, are displaced toward each other the engagement features 140*a*, 140*b* may interlock with each other.

Upon interlocking of the one curved portion 142*a* of the first resilient prong 120 and the two curved portions 142*b*, 142*c* of the second resilient prong 130, the one curved portion 142*a* of the first resilient prong 120 can be configured to be at least partially disposed at a position between the two curved portions 142*b*, 142*c* of the second resilient prong 130 (i.e., wherein the position comprises a gap or space between the two curved portions 142*b*, 142*c* of the engagement feature 140*b*).

FIG. 1C is a front view of a portion of the medical grasping device 100 of FIG. 1A. As depicted, the first resilient prong 120 comprises a concave proximal portion 126 and a convex distal portion 128. Likewise, the second resilient prong 130 comprises a concave proximal portion 136 and a convex distal portion 138. The concave proximal portions 126, 136 are concave with respect to the extension of the longitudinal axis 10 of the elongate member 110, and the concave proximal portions 126, 136 are positioned between the elongate member 110 and the convex distal portions 128, 138, respectively. The convex distal portions 128, 138 are convex with respect to the extension of the longitudinal axis 10 of the elongate member 110, and the convex distal portions 128, 138 extend from distal ends of the concave proximal portions 126, 136, respectively.

In some embodiments, the first resilient prong 120 and/or the second resilient prong 130 may comprise a first curve centered on a point outside of the first curve and a second curve centered on a point inside of the second curve. The radius of the first curve may be different from the radius of the second curve. Additionally, the first curve and the second curve may comprise a constant and/or a changing radius of curvature. In various embodiments, the first resilient prong 120 and/or the second resilient prong 130 may comprise an inflection point where the first resilient prong 120 and/or the second resilient prong 130 changes concavity.

In certain other embodiments, the first resilient prong may be curved (i.e., the first resilient prong may comprise a concave proximal portion and a distal convex portion); however, the second resilient prong may be substantially straight. For example, the second resilient prong may extend substantially parallel with respect to the extension of the longitudinal axis 10 of the elongate member 110 or the second resilient prong may extend, without significant curvature, at a substantially constant angle with respect to the extension of the longitudinal axis 10. The second resilient prong may also be configured to abut a luminal surface without significantly displacing and/or traumatizing the luminal surface. Such configurations of the first and second resilient prongs 120, 130 may allow or permit the substantially straight second resilient prong to be more easily displaced along or adjacent the luminal surface. Additionally, such a configuration of the first and second resilient prongs 120, 130 may allow or permit the substantially straight second resilient prong to be disposed in closer contact with the luminal surface in contrast to the curved first resilient prong which may extend away from the luminal surface. For example, if the target foreign object is closely embedded or engaged with the luminal surface, the straight resilient prong may be configured to engage or interact more easily with the target foreign object than the curved resilient prong.

In various embodiments, the medical grasping device 100 may further comprise a third resilient prong extending from the distal end 114 of the elongate member 110. Each of the first resilient prong, the second resilient prong, and the third resilient prong may extend from positions at the distal end 114 of the elongate member 110, and the positions may be substantially evenly spaced around a circumference of the elongate member 110. In various other embodiments, the medical grasping device may comprise four resilient prongs, wherein the four resilient prongs extend from the distal end 114 of the elongate member 110 and extend from positions at the distal end 114 of the elongate member 110 wherein the positions may be substantially evenly spaced around the circumference of the elongate member 110. Medical grasping devices comprising five, six, or more resilient prongs are also within the scope of this disclosure.

In some embodiments, components of the medical grasping device 100 may be integrally formed. For example, the elongate member 110 and the first and second resilient prongs 120, 130 may be integrally formed. In some other embodiments, components of the medical grasping device 100 may be discretely formed. For example, the elongate member 110 and the first and second resilient prongs 120, 130 may be discretely formed and subsequently coupled to each other.

Figure 2B:
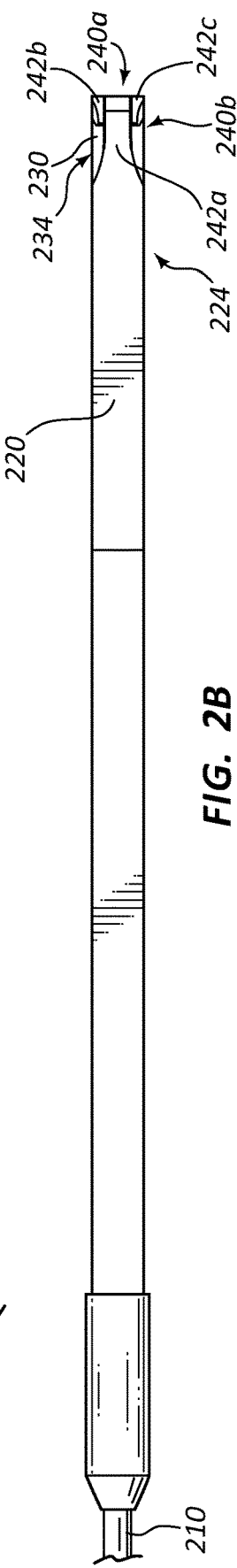
FIG. 2B is a side view of a portion of the medical grasping device of FIG. 2A.

FIGS. 2A and 2B illustrate another embodiment of a medical grasping device that can, in certain respects, resemble components of the medical grasping device described in connection with FIGS. 1A and 1B. It will be appreciated that all the illustrated embodiments may have analogous features. Accordingly, like features are designated with like reference numerals, with the leading digits incremented to "2." For instance, the elongate member is designated as "110" in FIGS. 1A and 1B, and an analogous elongate member is designated as "210" in FIGS. 2A and 2B. Relevant disclosure set forth above regarding similarly identified features thus may not be repeated hereafter. Moreover, specific features of the medical grasping device and related components shown in FIGS. 1A and 1B may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the medical grasping device of FIGS. 2A and 2B. Any suitable combination of the features, and variations of the same, described with respect to the medical grasping device and components illustrated in FIGS. 1A and 1B can be employed with the medical grasping device and components of FIGS. 2A and 2B, and vice versa. This pattern of disclosure applies equally to further embodiments depicted in subsequent figures and described hereafter.

The medical grasping device 200 of FIG. 2A comprises an elongate member 210. In some embodiments, the elongate member may be configured for displacement through a body lumen (e.g., a vessel of a patient). The medical grasping device 200 further comprises a plurality of resilient prongs extending from a distal end 214 of the elongate member 210. In the illustrated embodiment, the medical grasping device 200 comprises a first resilient prong 220 and a second resilient prong 230. Further, first and second engagement features 240a, 240b are coupled to distal ends 224, 234 of each of the first and second resilient prongs 220, 230. In some embodiments, each of the first and second resilient prongs 220, 230, respectively, and the first and second engagement features 240a, 240b are configured to secure a foreign object disposed within a body lumen.

A medical grasping device assembly may comprise a delivery sheath 250 disposed around at least a portion of the medical grasping device 200, such that the medical grasping device 200 is longitudinally displaceable within the delivery sheath 250. For example, the elongate member 210 and the medical grasping device 200 may be proximally and distally displaced within a lumen 252 of the delivery sheath 250. Upon proximal displacement of the plurality of resilient prongs into the lumen 252 of the delivery sheath 250, the first and second engagement features 240a, 240b can be displaced toward each other, and upon distal displacement of the plurality of resilient prongs out of the lumen 252 of the delivery sheath 250 the first and second engagement features 240a, 240b can be displaced away from each other. Stated another way, upon proximal displacement of the plurality of resilient prongs within or into the lumen 252 of the delivery sheath 250, a constraining force may be exerted on the first and second engagement features 240a, 240b, at least in part by the delivery sheath, such that the first and second engagement features 240a, 240b are displaced or moved toward each other.

Further, upon distal displacement of the plurality of resilient prongs away from or out of the lumen 252 of the delivery sheath 250 the constraining force may be removed from the first and second engagement features 240a, 240b such that the first and second engagement features 240a, 240b displace or move away from each other. In some embodiments, partial constraint of proximal portions of resilient prongs, similar to the first and second resilient prongs 220, 230, can cause displacement or movement of engagement features, similar to the first and second engagement features 240a, 240b, toward each other.

In some embodiments, upon proximal displacement of the first and second resilient prongs 220, 230 into the lumen 252 of the delivery sheath 250, the first engagement feature 240a may be configured to interlock with the second engagement feature 240b. The interlocking of the first engagement feature 240a and the second engagement feature 240b may be configured to secure a foreign object within a body lumen.

In certain embodiments, the medical grasping device 200 may further comprise an actuator (not shown) configured to alternatively displace the plurality of resilient prongs into and/or out of the lumen 252 of the delivery sheath 250. For example, the actuator may be configured to actuate the medical grasping device 200 such that the plurality of resilient prongs and/or the engagement features may engage and/or secure a foreign object within a body lumen. In various embodiments, the actuator may be spring loaded such that upon release of the actuator by a practitioner, the plurality of resilient prongs can be disposed within the lumen 252 of the delivery sheath 250. In various other embodiments, the actuator may be spring loaded such that upon release of the actuator by a practitioner, the plurality of resilient prongs can be displaced outside and distally from within the lumen 252 of the delivery sheath 250.

In the illustrated embodiment, the first engagement feature 240a comprises one curved portion 242a, wherein the curved portion 242a is disposed at the distal end 224 of the first resilient prong 220. Also, the second engagement feature 240b comprises two curved portions 242b, 242c, wherein the curved portions 242b, 242c are disposed at the distal end 234 of the second resilient prong 230. The curved portions 242a, 242b, 242c of the medical grasping device 200 are generally more tapered relative to the curved portions 142a, 142b, 142c of the medical grasping device 100 of FIGS. 1A and 1B. For example, a distal end of the curved portion 242a tapers to a wedge-like configuration or shape, whereas a distal end of the curved portion 142a is blunt relative to the distal end of the curved portion 242a. Additionally, distal ends of the curved portions 242b, 242c comprise tapered outside lateral sides while distal ends of the curved portions 142b, 142c comprise tapered inside lateral sides. Other configurations or shapes of the engagement features and/or curved portions are also contemplated. For example, the configurations or shapes of the engagement features and/or the curved portions may be designed for different purposes or uses. For example, engagement features and/or curved portions comprising a first shape may be better suited for the engagement and retrieval of a stent while engagement features and/or curved portions comprising a second shape may be better suited for engagement and retrieval of a vascular filter.

With continued reference to FIG. 2A, each of the first and second engagement features 240a, 240b comprises at least one curved portion 242a, 242b, 242c, wherein the at least one curved portion 242a, 242b, 242c curves inwardly toward an extension of a longitudinal axis 10 of the elongate member 210.

FIG. 2B is a side view of a portion of the medical grasping device 200 of FIG. 2A. In the illustrated embodiment, the position of the first resilient prong 220 relative to the position of the second resilient prong 230 is shown. The first engagement feature 240a can be disposed at the distal end 224 of the first resilient prong 220. Likewise, the second engagement feature 240b can be disposed at the distal end 234 of the second resilient prong 230. Additionally, the first engagement feature 240a comprises one curved portion 242a, wherein the curved portion 242a is disposed at the distal end 224 of the first resilient prong 220. Also, the second engagement feature 240b comprises two curved portions 242b, 242c, wherein the curved portions 242b, 242c are disposed at the distal end 234 of the second resilient prong 230. As described above, the one curved portion 242a of the first resilient prong 220 is configured to interlock or engage with the two curved portions 242b, 242c of the second resilient prong 230 when the distal ends 224, 234 of the first and second resilient prongs 220, 230, respectively, are displaced toward each other. Upon interlocking of the one curved portion 242a of the first resilient prong 220 and the two curved portions 242b, 242c of the second resilient prong 230, the one curved portion 242a of the first resilient prong 220 can be configured to be at least partially disposed at a position (i.e., in a gap or space) between the two curved portions 242b, 242c of the second resilient prong 230.

Figure 3B:
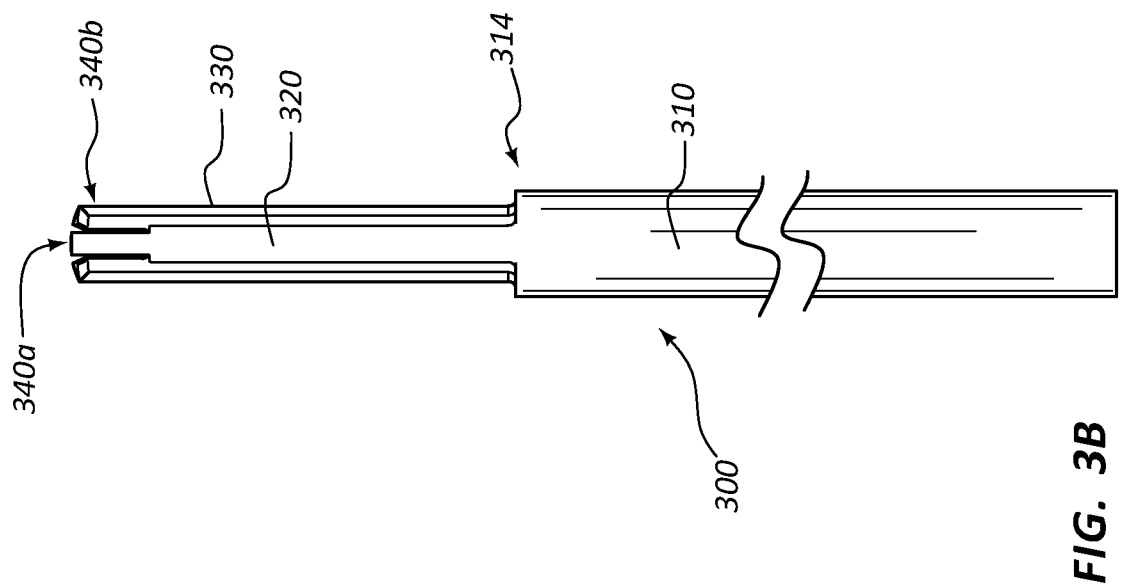
FIG. 3B is a side view of the medical grasping device of FIG. 3A.
Figure 3A:
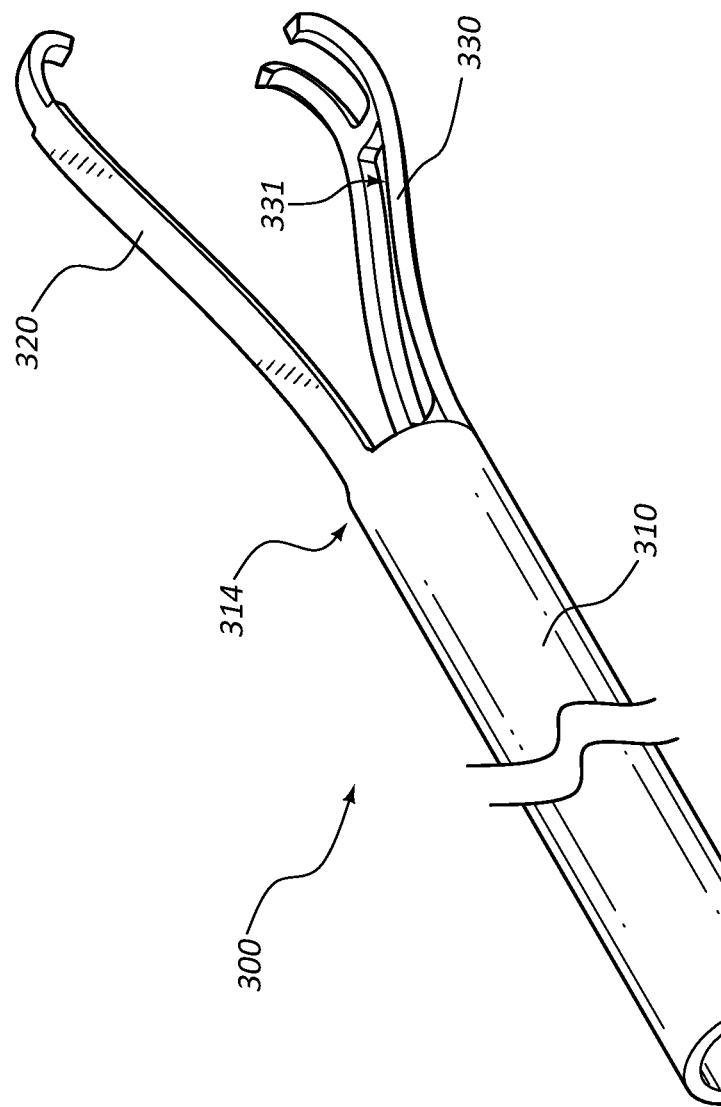
FIG. 3A is a perspective view of yet another embodiment of a medical grasping device.

FIG. 3A illustrates yet another embodiment of a medical grasping device 300. The medical grasping device 300 also comprises an elongate member 310. A cross-section of the elongate member 310 can be substantially circular. In some embodiments, however, the cross-section of the elongate member 310 may be substantially ovoid, square, triangular, or otherwise shaped. The medical grasping device 300 further comprises a first resilient prong 320 and a second resilient prong 330, wherein each of the first resilient prong 320 and the second resilient prong 330 is coupled to and extend from a distal end 314 of the elongate member 310.

The second resilient prong 330 of the illustrated embodiment further comprises a window or opening 331 extending longitudinally through at least a portion of the second resilient prong 330. As depicted, the first resilient prong 320 is generally narrower than the second resilient prong 330. The window 331 of the second resilient prong 330 may result in a second resilient prong 330 that comprises a substantially similar flexibility or resiliency to the flexibility or resiliency of the first resilient prong 320. The opening 331 may compensate for the greater width of the second resilient prong 330 relative to the first resilient prong 320. For example, the window 331 disposed through the wider second resilient prong 330 may generate or result in a second resilient prong 330 that comprises substantially comparable or equal amounts of material as the narrower first resilient prong 320, and as such the first and second resilient prongs 320, 330 may comprise substantially similar flexibilities or resiliencies.

A cross-section of each of the first resilient prong 320 and the second resilient prong 330 can be substantially semicircular. In some other embodiments, however, the cross-sections of the first and second resilient prongs 320, 330 may be substantially linear, L-shaped, or otherwise shaped. In some embodiments, a medical grasping device may be cut from a tube of a shape memory alloy. For example, the medical grasping device 300 may be cut from a tube of NITINOL and formed (i.e., be heat set) such that the first resilient prong 320 and the second resilient prong 330 are configured to move away from each other upon displacement of the medical grasping device out of a lumen of a delivery sheath. In some other embodiments, a medical grasping device may be milled from a block of material (i.e., a block of a metal).

FIG. 3B is a side view of the medical grasping device 300 of FIG. 3A. As illustrated, the medical grasping device 300 comprises the elongate member 310 and first and second resilient prongs 320, 330 coupled to and extending from the distal end 314 of the elongate member 310. From this view, the alignment of the first and second resilient prongs 320, 330 and their associated first and second engagement features 340a, 340b, respectively, can be seen. The first and second engagement features 340a, 340b, similar to the engagement features discussed above, can be configured to interlock with each other (i.e., via curved portions).

Figure 4E:
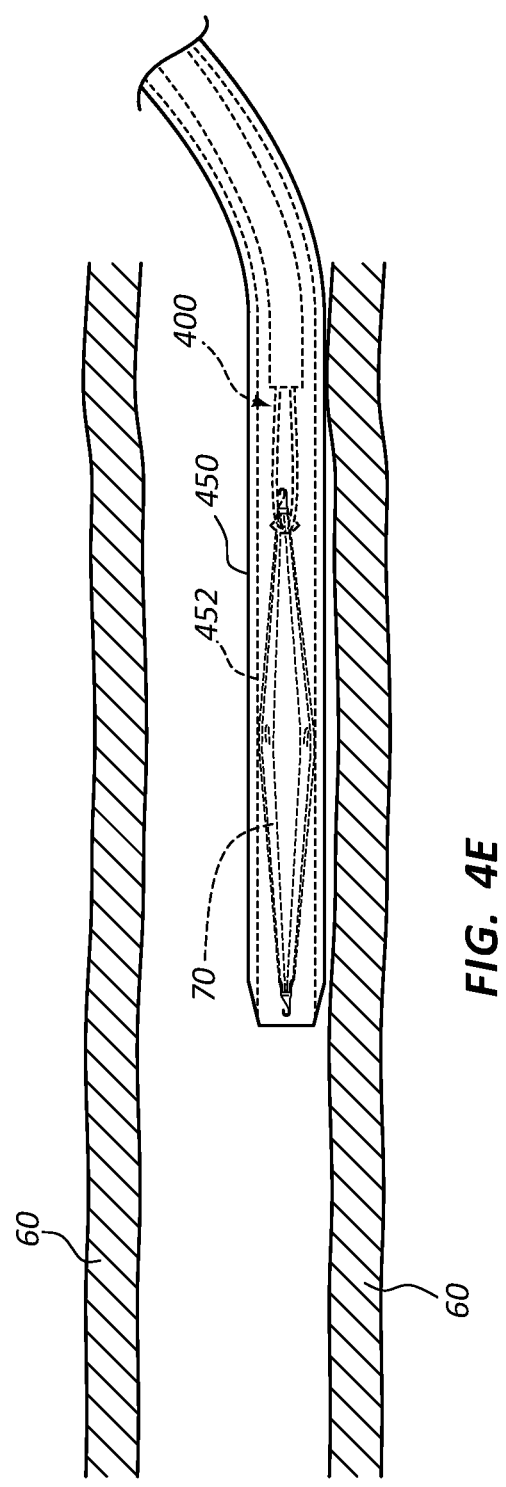
FIG. 4E is a side view of the medical grasping device assembly of FIG. 4A wherein the medical grasping device and the secured vascular filter have been disposed within the lumen of the delivery sheath.

FIGS. 4A-4E depict an illustrative method of using a medical grasping device assembly of the present disclosure to retrieve a target foreign object (e.g., a vascular filter, as illustrated) from a body lumen (e.g., a vessel as illustrated) of a patient. Although FIGS. 4A-4E depict a method of retrieving the vascular filter 70 from the vessel 60, methods of using the medical grasping device assembly of the present disclosure may also comprise methods of retrieving any target foreign object from within any body lumen. FIG. 4A is a side view of an embodiment of a medical grasping device assembly disposed with a lumen 62 of the vessel 60. The medical grasping device assembly comprises a grasping device 400, or medical grasping device, disposed within a lumen 452 of a delivery sheath 450. The method of retrieving the vascular filter 70, or the target foreign object, can comprise disposing the grasping device 400 and at least a distal end of the delivery sheath 450 to a position within the vessel 60 at or adjacent the vascular filter 70. As depicted, the grasping device 400 comprises an elongate member 410 and a plurality of resilient prongs, wherein each of the plurality of resilient prongs is coupled to and extends from a distal end 414 of the elongate member 410. Further, at least one engagement feature 440a, 440b can be disposed at distal ends 424, 434 of each of the first and second resilient prongs 420, 430, respectively. In some embodiments, as described above, the engagement features 440a, 440b may be configured to interlock to secure the vascular filter 70, or target foreign object. The target foreign object 70 can be selected from at least one of, but not limited to, a stent, a vascular filter, an embolus, or a bolus.

FIG. 4B is a side view of the medical grasping device assembly of FIG. 4A wherein the first and second resilient prongs 420, 430 of the medical grasping device 400 are at least partially distally displaced from within the lumen 452 of the delivery sheath 450. FIG. 4C is a side view of the medical grasping device assembly of FIG. 4A wherein the first and second resilient prongs 420, 430 of the medical grasping device 400 are fully displaced from within the lumen 452 of the delivery sheath 450. As depicted in FIGS. 4B and 4C, a method of retrieving the vascular filter 70, or target foreign object, can also comprise engaging at least one of the engagement features 440a, 440b with at least a portion of the vascular filter 70. For example, at least one of the engagement features 440a, 440b may contact at least a portion of the vascular filter 70 or at least one of the engagement features 440a, 440b may enter a space or volume defined by an outermost boundary of components of the vascular filter 70.

In some embodiments, a method of retrieving the target foreign object can further comprise actuating the grasping device 400 such that at least two of the engagement features 440a, 440b interlock with each other to secure the engaged target foreign object. In various embodiments, the method of retrieving the target foreign object can also comprise longitudinally displacing the grasping device 400 to dislodge or free the secured target foreign object from a position within a body lumen. For example, the grasping device may be displaced proximally toward a practitioner to dislodge the target foreign object from the body lumen. In some circumstances, tissue ingrowth may be disposed around at least a portion of the target foreign object. As used herein, the term "tissue ingrowth" refers to tissue at or adjacent a target foreign object that has grown in and/or around at least a portion of the target foreign object. The practitioner may increase a longitudinal force applied both proximally and distally upon the secured target foreign object to dislodge or free the target foreign object from the tissue ingrowth.

FIG. 4D is a side view of the medical grasping device assembly of FIG. 4A wherein the medical grasping device 400 has secured the vascular filter 70. In the illustrated embodiment, the practitioner may proximally displace the plurality of resilient prongs within the lumen 452 of the delivery sheath 450. The delivery sheath 450 can be disposed around at least a portion of the grasping device 400, and upon proximal displacement of the plurality of resilient prongs within the lumen 452 of the delivery sheath 450, an interaction between at least a portion of the delivery sheath 450 and the plurality of resilient prongs may act to displace each of the plurality of resilient prongs toward each other. Further, as depicted, the at least two engagement features 440a, 440b can interlock prior to displacement, or complete displacement, of the plurality of resilient prongs within the lumen 452 of the delivery sheath 450. The interlocking of the at least two engagement features 440a, 440b may secure the vascular filter 70 such that the vascular filter 70 may be displaced by the grasping device 400 within the lumen 452 of the delivery sheath 450. Thus, the vascular filter 70 may be secured by the medical grasping device 400 such that the vascular filter 70 is encircled by the medical grasping device 400 before a force is exerted on the vascular filter 70. This can allow or permit securement of the vascular filter 70 without, or with decreased, trauma to the vessel 60 or other body part, as the steps of securing the vascular filter 70 may be executed without displacing the vascular filter 70. In other words, the process of securing the vascular filter 70 may not disturb the placement of the vascular filter 70. In turn, this may facilitate a more controlled eventual displacement of the vascular filter 70 as the vascular filter 70 may be coupled to the medical grasping device 400 during any displacement of the vascular filter 70.

FIG. 4E is a side view of the medical grasping device assembly of FIG. 4A wherein the medical grasping device 400 and the secured vascular filter 70 have been disposed within the lumen 452 of the delivery sheath 450. As illustrated, the method can further comprise disposing the secured target foreign object 70 within the lumen 452 of the delivery sheath 450. In certain embodiments, the method may also comprise removing or retrieving each of the delivery sheath 450, the grasping device 400, and the secured target foreign object 70 from the body lumen 60 of the patient.

FIGS. 5A-5C illustrate another embodiment of a medical grasping device 500. As with the other embodiments disclosed herein, the embodiment of FIGS. 5A-5C may have analogous features to other embodiments. Disclosure set forth above with respect to these other embodiments, for example the embodiment of FIGS. 1A-1C, may thus be analogously applied to the embodiment of FIGS. 5A-5C.

FIGS. 5A and 5B illustrate an embodiment of a medical grasping device 500 in an open configuration. FIG. 5C illustrates the medical grasping device of FIGS. 5A and 5B in a closed configuration. As depicted, the medical grasping device 500 can comprise an elongate member 510. The medical grasping device 500 may also comprise at least two resilient prongs 520, 530. In the illustrated embodiment, the medical grasping device 500 comprises a first resilient prong 520 and a second resilient prong 530. In other embodiments, the medical grasping device 500 may comprise three resilient prongs, four resilient prongs, or more resilient prongs. The first and second resilient prongs 520, 530 are coupled to the elongate member 510 at a distal end 514 of the elongate member 510, and each of the first and second resilient prongs 520, 530 can extend distally from the distal end 514 of the elongate member 510.

At least one engagement feature 540a may be disposed at a distal end 524 of the first resilient prong 520. Likewise, at least one engagement feature 540b may be disposed at a distal end 534 of the second resilient prong 530. In the illustrated embodiment, the engagement feature 540a comprises one curved portion 542a, wherein the curved portion 542a is disposed at the distal end 524 of the first resilient prong 520. Also, as illustrated, the engagement feature 540b comprises two curved portions 542b, 542c, wherein the two curved portions 542b, 542c are disposed at the distal end 534 of the second resilient prong 530. The one curved portion 542a of the first resilient prong 520 may be configured to interlock or engage with the two curved portions 542b, 542c of the second resilient prong 530 when the distal ends 524, 534 of the first and second resilient prongs 520, 530, respectively, are displaced toward each other (as discussed in further detail below). The interlocking of the curved portions 542a, 542b, 542c may be configured to secure a target foreign object disposed within a body lumen. For example, a target foreign object may be secured before any force is applied on the target foreign object by a medical grasping device. Such a configuration may facilitate a traumatic, or less traumatic, securement of the target foreign object prior to displacement of the target foreign object.

With comparison to the embodiment of FIGS. 1A-1C, the medical grasping device 500 of FIGS. 1A-1C, the curved portion 542a further comprises a distal lip 542a'. The distal lip 542a' may be configured to contact with an interior portion distal portion 534 of the second resilient prong 530. As shown in FIG. 5C, contact between the distal lip 542a' and the distal portion 534 of the second resilient prong 530 may provide a positive stop for relative displacement between the first resilient arm 520 and the second resilient arm 530. This positive stop may prevent over extension of the first resilient prong 520 and second resilient prong 530 and/or may prevent the curved portion 542a from passing through the two curved portions 542b, 542c of the second resilient prong 530 and catching on an exterior surface of the second resilient prong 530.

As discussed above, the first resilient prong 520 and second resilient prong 530 may be constrained within the sheath or catheter when in a closed configuration, such as that of FIG. 5C. When in such a closed configuration, constraints on the curved resilient prongs 520, 530 may thus result in a grasping or closing force acting on the resilient prongs 520, 530. The positive stop provided by the distal lip 542a' may prevent the distal ends of the resilient prongs 520, 530 from over-extension, such as by preventing the distal ends of the resilient prongs 520, 530 from crossing each other. This may, in turn, prevent the resilient prongs 520, 530 from catching in a closed position, for example, by preventing the first engagement feature 542a from snapping past the second resilient prong 530 and engagement with an exterior surface of the second resilient prong 530. Such engagement could potentially prevent the medical grasping device 500 from reopening once the constraining force is removed.

Also as compared to the embodiment of FIGS. 1A-1C, the first resilient prong 520 and the second resilient prong 530 may comprise a different curvature. Various scales, sizes, and curvatures of resilient prongs are within the scope of this disclosure. As with other embodiments disclosed herein, the first resilient prong 520 and the second resilient prong 530 may be laser cut from a single piece of material or may be stamped from a single material and coupled together with a collar or other coupling member.

With reference to FIG. 5A, each of the first resilient prong 520 and the second resilient prong 530 curves outwardly from an extension of a longitudinal axis 12 of the elongate member 510. In contrast, each of the curved portions 542a, 542b, 542c curves inwardly toward the extension of the longitudinal axis 12 of the elongate member 510. Again, this shape and curvature may differ from other embodiments, such as the embodiment of FIGS. 1A-1C.

As depicted, each of the first resilient prong 520 and the second resilient prong 530 extends from the distal end 514 of the elongate member 510 such that the first resilient prong 520 extends in a substantially opposite direction from the second resilient prong 530. Stated another way, the extension of the first resilient prong 520 from the elongate member 510 generates or forms a substantially mirror image of the extension of the second resilient prong 530 from the elongate member 510, and vice versa. As illustrated, the first resilient prong 520 extends from a first portion at the distal end 514 of the elongate member 510 and the second resilient prong 530 extends from a second portion at the distal end 514 of the elongate member 510, wherein the first position and the second position are disposed at substantially opposite positions along a circumference of the distal end 514 of the elongate member 510. As such, each of the first resilient prong 520 and the second resilient prong 530 is substantially disposed within a single plane. Other dispositions of the first and second resilient prongs 520, 530 around the circumference of the distal end 514 of the elongate member are also within the scope of this disclosure.

FIG. 5B is a side view of a portion of the medical grasping device 500 of FIG. 5A, with the medical grasping device disposed in an open configuration as in FIG. 5A. In the illustrated embodiment, the relative position of the first resilient prong 520 in relation to the position of the second resilient prong 530 is shown. As described above, at least one engagement feature 540a can be disposed at the distal end 524 of the first resilient prong 520. Likewise, at least one engagement feature 540b may be disposed at the distal end 534 of the second resilient prong 530. The engagement feature 540a of the first resilient prong 520, as illustrated, comprises one curved portion 542a, wherein the curved portion 542a is disposed at the distal end 524 of the first resilient prong 520. The engagement feature 540b of the second resilient prong 530 comprises two curved portions 542b, 542c, wherein the curved portions 542b, 542c are disposed at the distal end 534 of the second resilient prong 530. The distal lip 542a' of the curved portion 542a of the first resilient prong 520 is also shown. As depicted, the one curved portion 542a of the first resilient prong 520 is configured to interlock with or engage with the two curved portions 542b, 542c of the second resilient prong 530. For example, when the distal ends 524, 534 of the first and second resilient prongs 520, 530, respectively, are displaced toward each other the engagement features 540a, 540b may interlock with each other. The distal lip 542a' may provide a positive stop as described above.

Upon interlocking of the one curved portion 542a of the first resilient prong 520 and the two curved portions 542b, 542c of the second resilient prong 530, the one curved portion 542a of the first resilient prong 520 can be configured to be at least partially disposed at a position between the two curved portions 542b, 542c of the second resilient prong 530 (i.e., wherein the position comprises a gap or space between the two curved portions 542b, 542c of the engagement feature 540b). Again, the distal lip 542a' may provide a positive stop though interaction with the second resilient prong 530, preventing over-extension of the first resilient prong 520 and second resilient prong 530 with respect to each other.

FIG. 5C is a front view of a portion of the medical grasping device 500 of FIG. 5A, with the first resilient prong 520 and the second resilient prong 530 disposed in a closed configuration. As depicted, the first resilient prong 520 comprises a concave proximal portion 526 and a convex distal portion 528. Likewise, the second resilient prong 530 comprises a concave proximal portion 536 and a convex distal portion 538. The concave proximal portions 526, 536 are concave with respect to the extension of the longitudinal axis 12 of the elongate member 510, and the concave proximal portions 526, 536 are positioned between the elongate member 510 and the convex distal portions 528, 538, respectively. The convex distal portions 528, 538 are convex with respect to the extension of the longitudinal axis 12 of the elongate member 510, and the convex distal portions 528, 538 extend from distal ends of the concave proximal portions 526, 536, respectively. As discussed above, in this closed configuration the distal lip 542a' is in contact with an interior surface of the distal portion 534 of the second resilient prong 530. This contact may provide a positive stop and may aid in preventing the first resilient prong 520 and second resilient prongs 530 from crossing each other when the medical grasping device 500 is constrained in a closed configuration.

In some embodiments, the first resilient prong 520 and/or the second resilient prong 530 may comprise a first curve centered on a point outside of the first curve and a second curve centered on a point inside of the second curve. The radius of the first curve may be different from the radius of the second curve. Additionally, the first curve and the second curve may comprise a constant and/or a changing radius of curvature. In various embodiments, the first resilient prong 520 and/or the second resilient prong 530 may comprise an inflection point where the first resilient prong 520 and/or the second resilient prong 530 changes concavity.

In certain other embodiments, the first resilient prong may be curved (i.e., the first resilient prong may comprise a concave proximal portion and a distal convex portion); however, the second resilient prong may be substantially straight. For example, the second resilient prong may extend substantially parallel with respect to the extension of the longitudinal axis 12 of the elongate member 110 or the second resilient prong may extend, without significant curvature, at a substantially constant angle with respect to the extension of the longitudinal axis 12. The second resilient prong may also be configured to abut a luminal surface without significantly displacing and/or traumatizing the luminal surface. Such configurations of the first and second resilient prongs 520, 530 may allow or permit the substantially straight second resilient prong to be more easily displaced along or adjacent the luminal surface. Additionally, such a configuration of the first and second resilient prongs 520, 530 may allow or permit the substantially straight second resilient prong to be disposed in closer contact with the luminal surface in contrast to the curved first resilient prong which may extend away from the luminal surface. For example, if the target foreign object is closely embedded or engaged with the luminal surface, the straight resilient prong may be configured to engage or interact more easily with the target foreign object than the curved resilient prong.

In various embodiments, the medical grasping device 500 may further comprise a third resilient prong extending from the distal end 514 of the elongate member 510. Each of the first resilient prong, the second resilient prong, and the third resilient prong may extend from positions at the distal end 514 of the elongate member 510, and the positions may be substantially evenly spaced around a circumference of the elongate member 510. In various other embodiments, the medical grasping device may comprise four resilient prongs, wherein the four resilient prongs extend from the distal end 514 of the elongate member 510 and extend from positions at the distal end 514 of the elongate member 510 wherein the positions may be substantially evenly spaced around the circumference of the elongate member 510. Medical grasping devices comprising five, six, or more resilient prongs are also within the scope of this disclosure.

Again, as discussed above, in some embodiments, components of the medical grasping device 500 may be integrally formed. For example, the elongate member 510 and the first and second resilient prongs 520, 530 may be integrally formed. In some other embodiments, components of the medical grasping device 500 may be discretely formed. For example, the elongate member 510 and the first and second resilient prongs 520, 530 may be discretely formed and subsequently coupled to each other.

FIGS. 6A-6D collectively illustrate another embodiment of a medical grasping device 600 that may, in certain respects, resemble components of the medical grasping device 100 described in connection with FIGS. 1A and 1B. It will be appreciated that all the illustrated embodiments may have analogous features. Accordingly, like features are designated with like reference numerals, with the leading digits incremented to "6." For instance, the elongate member is designated as "110" in FIGS. 1A and 1B, and an analogous elongate member is designated as "610" in FIGS. 6A-6D. Relevant disclosure set forth above regarding similarly identified features thus may not be repeated hereafter. Moreover, specific features of the medical grasping device and related components shown in FIGS. 1A and 1B may not be shown or identified by a reference numeral in FIGS. 6A-6D or specifically discussed in the written description that follows. However, such features may clearly be the same, or substantially the same, as features depicted in other embodiments and/or described with respect to such embodiments. Accordingly, the relevant descriptions of such features apply equally to the features of the medical grasping device of FIGS. 6A-6D. Any suitable combination of the features, and variations of the same, described with respect to the medical grasping device and components illustrated in FIGS. 1A and 1B can be employed with the medical grasping device and components of FIGS. 6A-6D, and vice versa.

Figure 6A:
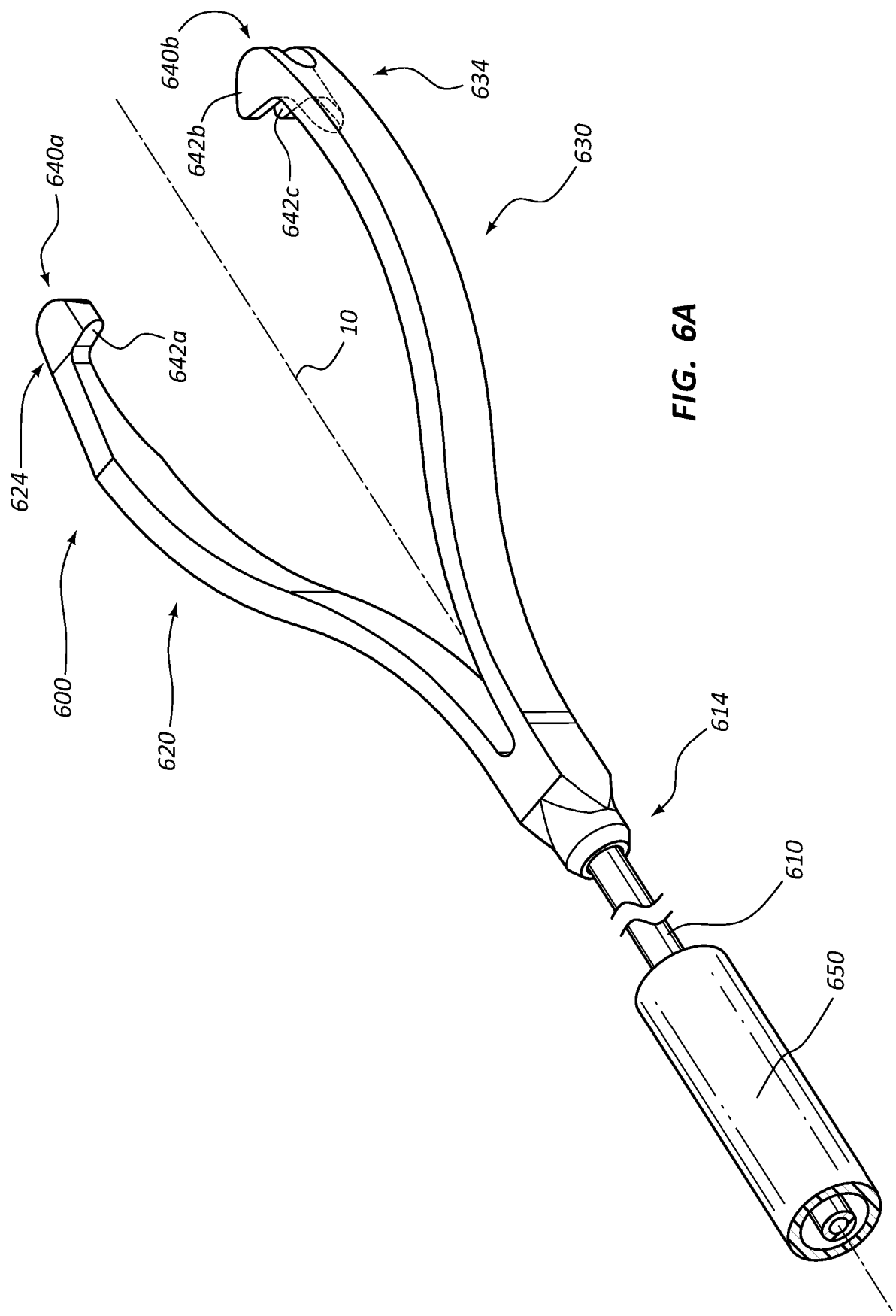
FIG. 6A is a first perspective view of another embodiment of a medical grasping device.
Figure 6B:
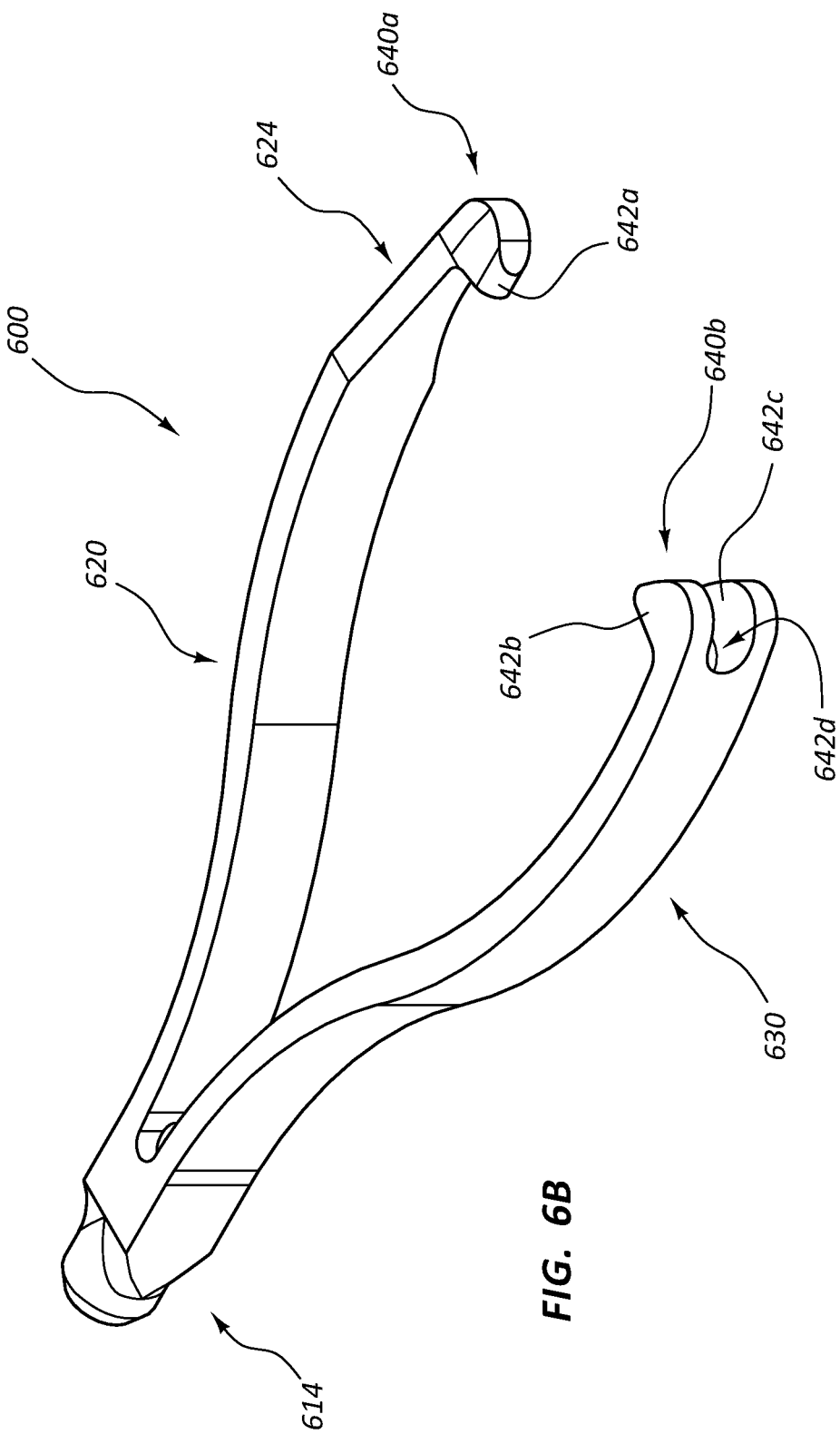
FIG. 6B is a second perspective view of the medical grasping device of FIG. 6A.

With reference to FIGS. 6A and 6B, the medical grasping device 600 comprises an elongate member 610, which, in some embodiments, may be configured for displacement through a body lumen (e.g., a vessel of a patient) in a similar fashion as described with reference to FIGS. 4A-4E. The medical grasping device 600 further comprises a plurality of resilient prongs extending from a distal end 614 of the elongate member 610. In the illustrated embodiment, the medical grasping device 600 comprises a first resilient prong 620 and a second resilient prong 630. In other embodiments, the medical grasping device 600 may comprise three resilient prongs, four resilient prongs, or more resilient prongs.

The first resilient prong 620 may include a first engagement feature 640*a* positioned at a distal end 624. Likewise, at least one second engagement feature 640*b* may be disposed at a distal end 634 of the second resilient prong 630. In some embodiments, the engagement features 640*a*, 640*b* may each be formed as integral components of the first and second resilient prongs 620, 630 respectively. In other embodiments, one or both of the engagement features 640*a*, 640*b* may instead be formed as standalone components affixed or otherwise coupled to the first and second resilient prongs 620, 630 respectively.

In the illustrated embodiment of FIGS. 6A and 6B, the engagement feature 640*a* comprises a protuberance 642*a* extending forwardly from the distal end 624 of the first resilient prong 620 and facing the second resilient prong 630. In some embodiments, the protuberance 642*a* may comprise a tooth, a hook, or any other suitable catch mechanism. In addition, the second engagement feature 640*b* may include two curved portions 642*b*, 642*c* disposed at the distal end 634 of the second resilient prong 630. As discussed in further detail below with particular reference to FIGS. 6C and 6D, the protuberance 642*a* of the first resilient prong 620 may be configured to interlock or engage with the two curved portions 642*b*, 642*c* of the second resilient prong 630 when the distal ends 624, 634 of the first and second resilient prongs 620, 630, respectively, are displaced toward each other. In some embodiments, upon interlocking of the protuberance 642*a* of the first resilient prong 620 and the two curved portions 642*b*, 642*c* of the second resilient prong 630, the protuberance 642*a* of the first resilient prong 620 may be configured to be at least partially disposed at a position between the two curved portions 642*b*, 642*c* of the second resilient prong 630. In some embodiments, the position may comprise a gap or space 642*d* formed between the two curved portions 642*b*, 642*c* of the engagement feature 640*b*. The interlocking of the protuberance 642*a* and the curved portions 642*b*, 642*c* may be configured to secure a foreign object disposed within a body lumen, such as a vascular filter 70 (see FIG. 4A). Additional details relating to the interlocking relationship of the first and second resilient prongs 620, 630 is described further below with particular reference to FIGS. 6C and 6D.

With continued reference to FIGS. 6A and 6B, each of the first resilient prong 620 and the second resilient prong 630 curves outwardly from an extension of a longitudinal axis 10 of the elongate member 610. In contrast, each of the protuberance 642*a* and the curved portions 642*b*, 642*c* curves inwardly toward the extension of the longitudinal axis 10 of the elongate member 610.

As depicted, each of the first resilient prong 620 and the second resilient prong 630 extends from the distal end 614 of the elongate member 610 such that the first resilient prong 620 extends in a substantially opposite direction from the second resilient prong 630. Stated another way, the extension of the first resilient prong 620 from the elongate member 610 generates or forms a substantially mirror image of the extension of the second resilient prong 630 from the elongate member 610, and vice versa. As illustrated, the first resilient prong 620 extends from a first portion at the distal end 614 of the elongate member 610 and the second resilient prong 630 extends from a second portion at the distal end 614 of the elongate member 610, wherein the first portion and the second portion are disposed at substantially opposite positions along a circumference of the distal end 614 of the elongate member 610. As such, each of the first resilient prong 620 and the second resilient prong 630 is substantially disposed within a single plane. Other dispositions of the first and second resilient prongs 620, 630 around the circumference of the distal end 614 of the elongate member are also within the scope of this disclosure.

FIG. 6C is a front view of a portion of the medical grasping device 600 of FIG. 6A in an open configuration. As depicted, the first resilient prong 620 comprises a concave proximal portion 626 and a convex distal portion 628. Likewise, the second resilient prong 630 comprises a concave proximal portion 636 and a convex distal portion 638. The concave proximal portions 626, 636 are concave with respect to the extension of the longitudinal axis 10 of the elongate member 610, and the concave proximal portions 626, 636 are positioned between the elongate member 610 and the convex distal portions 628, 638, respectively. The convex distal portions 628, 638 are convex with respect to the extension of the longitudinal axis 10 of the elongate member 610, and the convex distal portions 628, 638 extend from distal ends of the concave proximal portions 626, 636, respectively.

In some embodiments, the first resilient prong 620 and/or the second resilient prong 630 may comprise a first curve centered on a point outside of the first curve and a second curve centered on a point inside of the second curve. The radius of the first curve may be different from the radius of the second curve. Additionally, the first curve and the second curve may comprise a constant and/or a changing radius of curvature. In various embodiments, the first resilient prong 620 and/or the second resilient prong 630 may comprise an inflection point where the first resilient prong 620 and/or the second resilient prong 630 changes concavity.

As depicted in FIG. 6C, the protuberance 642*a* of the first resilient prong 620 includes a retaining face 643*a* formed along a bottom surface of the protuberance 642*a*, the retaining face 643*a* positioned on a downward-facing portion of the protuberance 642*a* oriented toward the distal end 614 of the elongate member 610. Likewise, the curved portions 642*b*, 642*c* of the second resilient prong 630 also include a retaining face 643*b* (the retaining face for the curved portion 642*c* is obscured from view in FIG. 6C) formed along a bottom surface of the respective curved portions 642*b*, 642*c*. When the medical grasping device 600 is at rest in the open configuration, the retaining faces 643*a*, 643*b* are each angled or sloped with respect to the extension of the longitudinal axis 10 of the elongate member 610. The sloped or angled retaining faces 643*a*, 643*b* may promote easier release and repositioning of the medical grasping device 600 during use.

In some embodiments, the retaining faces 643*a*, 643*b* may be angled or sloped to form obtuse angles $\alpha$ and $\beta$, respectively when the medical grasping device 600 is in an open configuration as illustrated in FIG. 6C. For example, in some embodiments, the angles $\alpha$ and $\beta$ may each be approximately 95 degrees when the medical grasping device 600 is in the open configuration. In other embodiments, the angles α and β may range from between 90 degrees to 100 degrees. In still other embodiments, the angles α and β may range between 90 degrees to 120 degrees. Although the above description provides certain ranges for angles α and β, it should be understood that the angles α and β of the retaining faces 643a, 643b may include any obtuse angle, that is, any angle greater than 90 degrees.

FIG. 6D is a front view of a portion of the medical grasping device 600 of FIG. 6A in a closed configuration. The following description provides additional details relating to the bending action of the first and second resilient prongs 620, 630 as the medical grasping device 600 is urged toward the interlocked and closed configuration by the delivery sheath 650. With collective reference to FIGS. 6C and 6D, as the first and second resilient prongs 620, 630 are retracted into the delivery sheath 650, the prongs 620, 630 are urged to move toward the longitudinal axis 10, thereby drawing the protuberance 642a and the curved portions 642b, 642c toward one another. As the protuberance 642a and the curved portions 642b, 642c move toward the longitudinal axis 10, the angle of the respective retaining faces 643a, 643b gradually or incrementally changes from its initial obtuse angle (e.g., angles α and β of FIG. 6C) and down toward a final acute angle to improve the gripping characteristics of the medical grasping device 600 in the closed configuration.

For example, with reference to FIG. 6D, when the medical grasping device 600 is in the closed position, the retaining face 643b forms an acute angle Θ with respect to the longitudinal axis 10. Likewise, the retaining face 643a of the protuberance 642a also forms an acute angle (not shown to avoid obscuring pertinent details, but it may be substantially equal to acute angle Θ). In some embodiments, the acute angle Θ may range from between 80 degrees to 90 degrees, while in other embodiments, the acute angle Θ may range from between 60 degrees to 85 degrees. Although the above description provides certain ranges for angle Θ, it should be understood that the angle Θ of the retaining faces 643a, 643b in the closed configuration may include any acute angle, that is, any angle less than 90 degrees.

In various embodiments, the medical grasping device 600 may further comprise a third resilient prong extending from the distal end 614 of the elongate member 610. Each of the first resilient prong, the second resilient prong, and the third resilient prong may extend from positions at the distal end 614 of the elongate member 610, and the positions may be substantially evenly spaced around a circumference of the elongate member 610. In various other embodiments, the medical grasping device may comprise four resilient prongs, wherein the four resilient prongs extend from the distal end 614 of the elongate member 610 and extend from positions at the distal end 614 of the elongate member 610 wherein the positions may be substantially evenly spaced around the circumference of the elongate member 610. Medical grasping devices comprising five, six, or more resilient prongs are also within the scope of this disclosure.

Again, as discussed above, in some embodiments, components of the medical grasping device 600 may be integrally formed. For example, the elongate member 610 and the first and second resilient prongs 620, 630 may be integrally formed. In some other embodiments, components of the medical grasping device 600 may be discretely formed. For example, the elongate member 610 and the first and second resilient prongs 620, 630 may be discretely formed and subsequently coupled to each other.

Figure 6E:
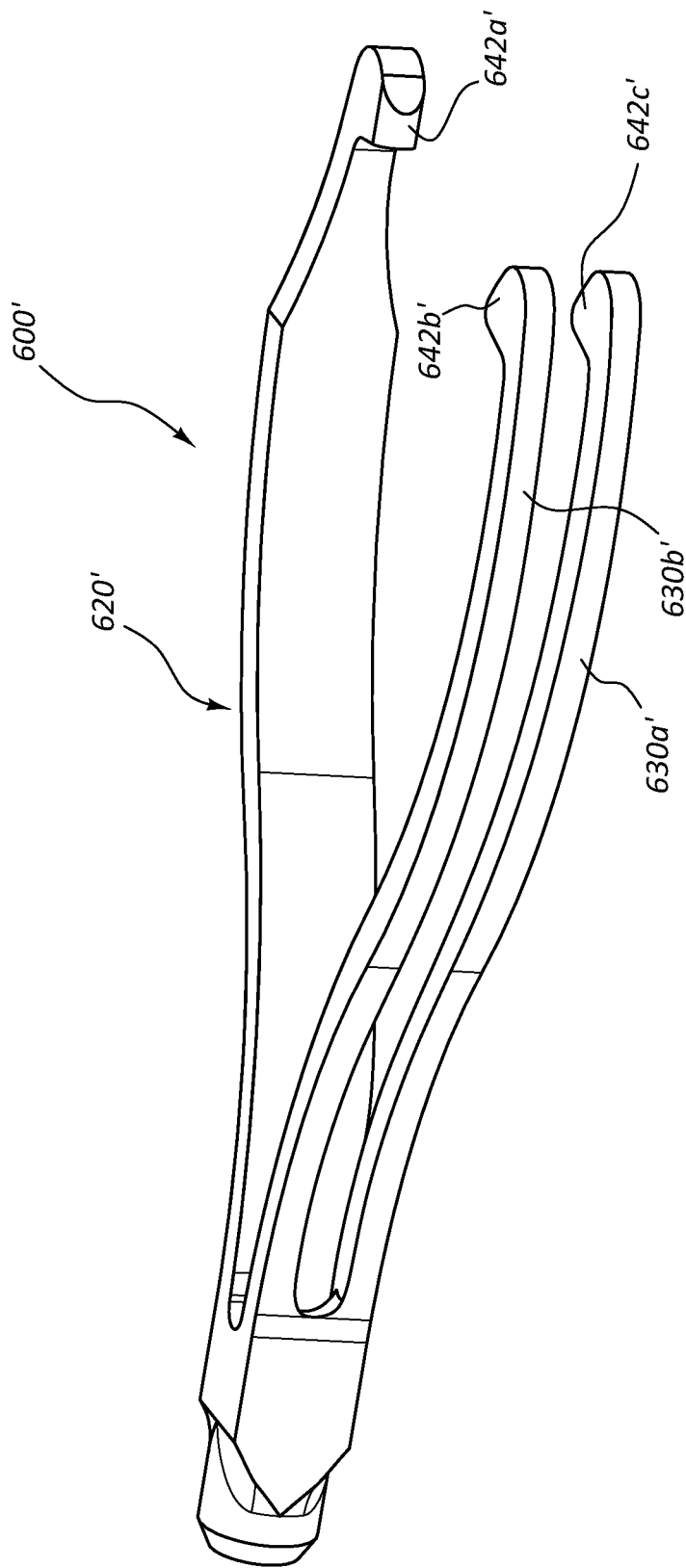
FIG. 6E is a perspective view of another embodiment of a medical grasping device.
Figure 6F:
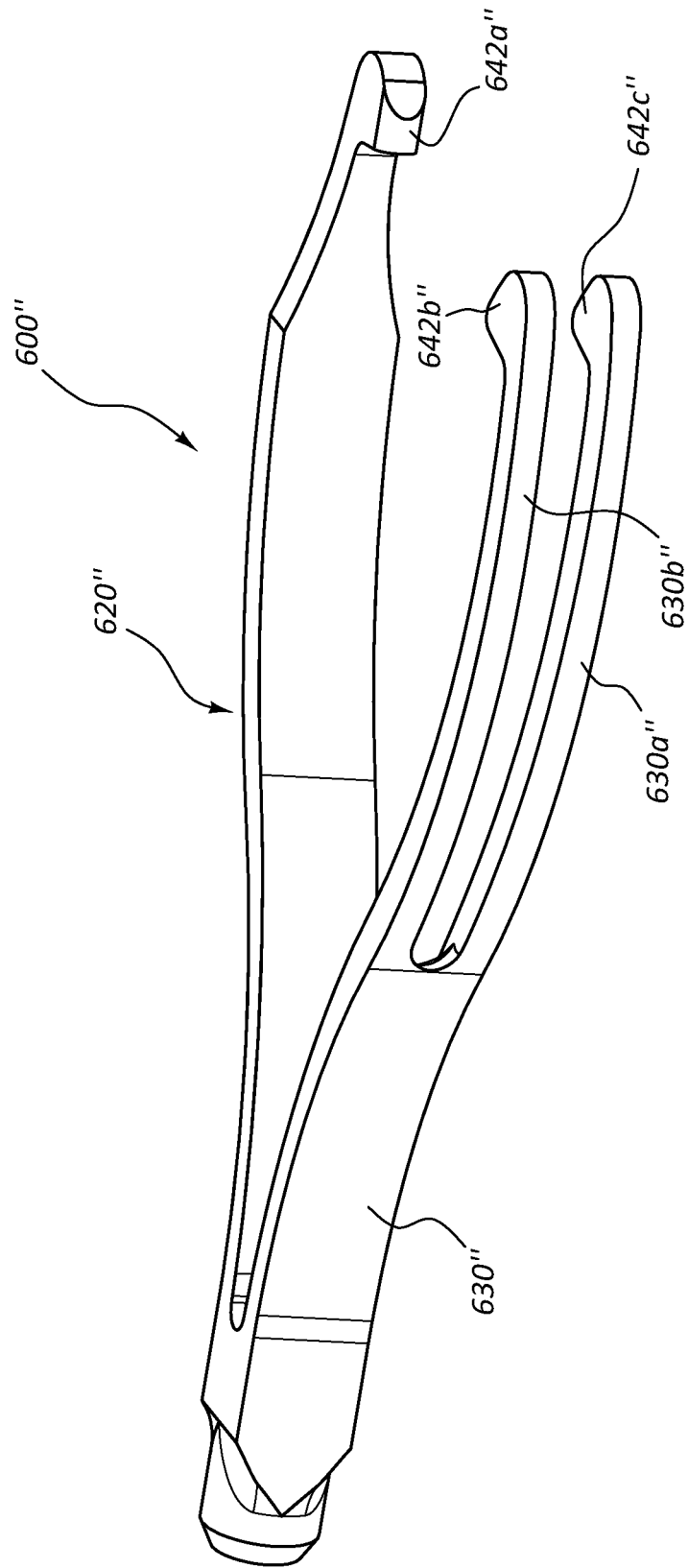
FIG. 6F is a perspective view of another embodiment of a medical grasping device.

FIGS. 6E and 6F are views of two additional embodiments of medical grasping devices 600' and 600". The medical grasping devices 600', 600" may resemble the medical grasping device 600 of FIGS. 6A-6D and disclosure recited in connection with the medical grasping device 600 of FIGS. 6A-6D analogously applies to the embodiments of FIGS. 6E and 6F.

As compared to the embodiment of FIGS. 6A-6D, the medical grasping device 600' of FIG. 6E comprises a first resilient prong 620' disposed opposite of two secondary resilient prongs 630a' and 630b'. In other words, the embodiment of FIG. 6E illustrates one embodiment of a medical grasping device 600' having three resilient prongs 620', 630a', 630b'. In other embodiments within the scope of this disclosure, the medical grasping device may have four, five, six, or more resilient prongs, including embodiments wherein each prong is disposed at 180 degree to another prong, and embodiments wherein the prongs are spaced at other intervals.

In the embodiment of FIG. 6F, the medical grasping device 600" comprises a first resilient prong 620" disposed opposite of a second resilient prong 630". In this embodiment, the second resilient prong 630" splits into a first leg 630a" and a second leg 630b" at a point between the proximal end of the second resilient prong 630" curved portions 642b" and 642c". Embodiments wherein one or more resilient prongs split along the length of the prong are likewise within the scope of this disclosure.

In the embodiments of FIGS. 6E and 6F, the protuberances 642a', 642a" and the two curved portions 642b', 642b", 642c', 642c" may interact in the same manner as discussed in connection with the protuberance 642a and curved portions 642b, 642c of the embodiment of FIGS. 6A-6D.

Additionally, though the embodiments of FIGS. 6E and 6F are variants of the embodiment of FIGS. 6A-6D, with additional resilient prongs, it is within the scope of this disclosure to modify the other embodiments disclosed herein with three, four, five, or more resilient prongs.

FIGS. 7A-7D collectively illustrate another embodiment of a medical grasping device 700 that may, in certain respects, resemble components of the medical grasping device described in connection with FIGS. 1A and 1B. It will be appreciated that all the illustrated embodiments may have analogous features. Accordingly, like features are designated with like reference numerals, with the leading digits incremented to "7." For instance, the elongate member is designated as "110" in FIGS. 1A and 1B, and an analogous elongate member is designated as "710" in FIGS. 7A-7D. Relevant disclosure set forth above regarding similarly identified features thus may not be repeated hereafter. Moreover, specific features of the medical grasping device and related components shown in FIGS. 1A and 1B may not be shown or identified by a reference numeral in FIGS. 7A-7D or specifically discussed in the written description that follows. However, such features may clearly be the same, or substantially the same, as features depicted in other embodiments and/or described with respect to such embodiments. Accordingly, the relevant descriptions of such features apply equally to the features of the medical grasping device of FIGS. 7A-7D. Any suitable combination of the features, and variations of the same, described with respect to the medical grasping device and components illustrated in FIGS. 1A and 1B can be employed with the medical grasping device and components of FIGS. 7A-7D, and vice versa.

The medical grasping device 700 of FIGS. 7A and 7B comprises an elongate member 710, which, in some embodiments, may be configured for displacement through a body lumen (e.g., a vessel of a patient) in a similar fashion as described with reference to FIGS. 4A-4E. The medical grasping device 700 further comprises a plurality of resilient prongs extending from a distal end 714 of the elongate member 710. In the illustrated embodiment, the medical grasping device 700 comprises a first resilient prong 720 and a second resilient prong 730. In other embodiments, the medical grasping device 700 may comprise three resilient prongs, four resilient prongs, or more resilient prongs.

The first resilient prong 720 may include a first engagement feature 740a positioned at a distal end 724. Likewise, at least one second engagement feature 740b may be disposed at a distal end 734 of the second resilient prong 730 In some embodiments, the engagement features 740a, 740b may each be formed as integral components of the first and second resilient prongs 720, 730 respectively. In other embodiments, one or both of the engagement features 740a, 740b may instead be formed as standalone components affixed or otherwise coupled to the first and second resilient prongs 720, 730 respectively.

In the illustrated embodiment, the engagement feature 740a comprises a protuberance 742a (such as a tooth, hook, or other catch) extending outwardly from the distal end 724 of the first resilient prong 720 and facing upwardly in a direction generally parallel to the longitudinal axis 10. In addition, the second engagement feature 740b may include two curved portions 742b, 742c at the distal end 734 of the second resilient prong 730, wherein the curved portions 742b, 742c include a slot or window 742d formed therebetween. As discussed in further detail below with particular reference to FIGS. 7C and 7D, the protuberance 742a of the first resilient prong 720 may be configured to interlock or engage with the slot or window 742d between the two curved portions 742b, 742c of the second resilient prong 730 when the distal ends 724, 734 of the first and second resilient prongs 720, 730, respectively, are displaced toward each other. The interlocking of the protuberance 742a and the curved portions 742b, 742c may be configured to secure a foreign object disposed within a body lumen, such as a vascular filter 70 (see FIG. 4A). Additional details relating to the interlocking relationship of the first and second resilient prongs 720, 730 is described further below with particular reference to FIGS. 7C and 7D.

Figure 7A:
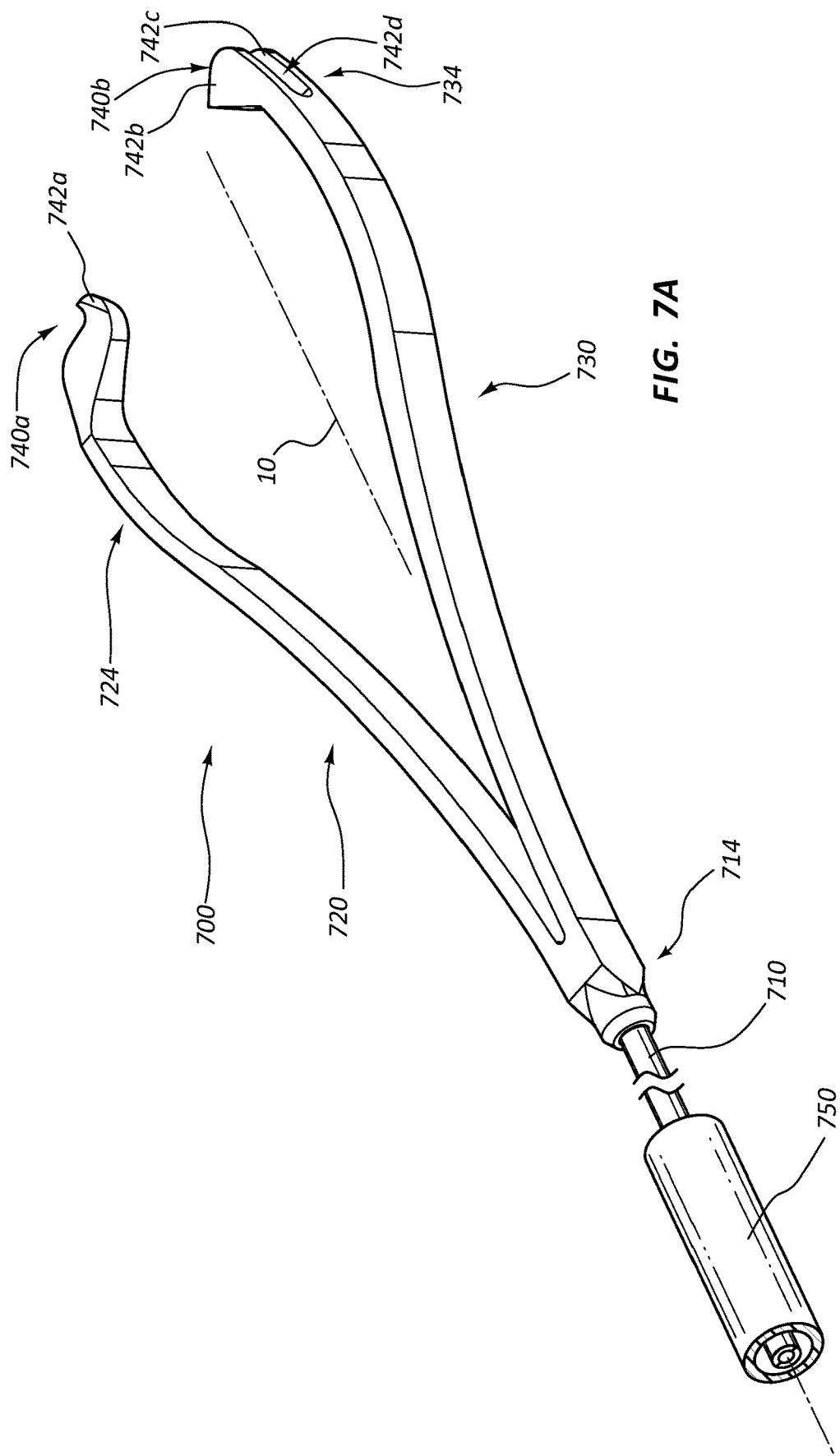
FIG. 7A is a first perspective view of another embodiment of a medical grasping device.
Figure 7B:
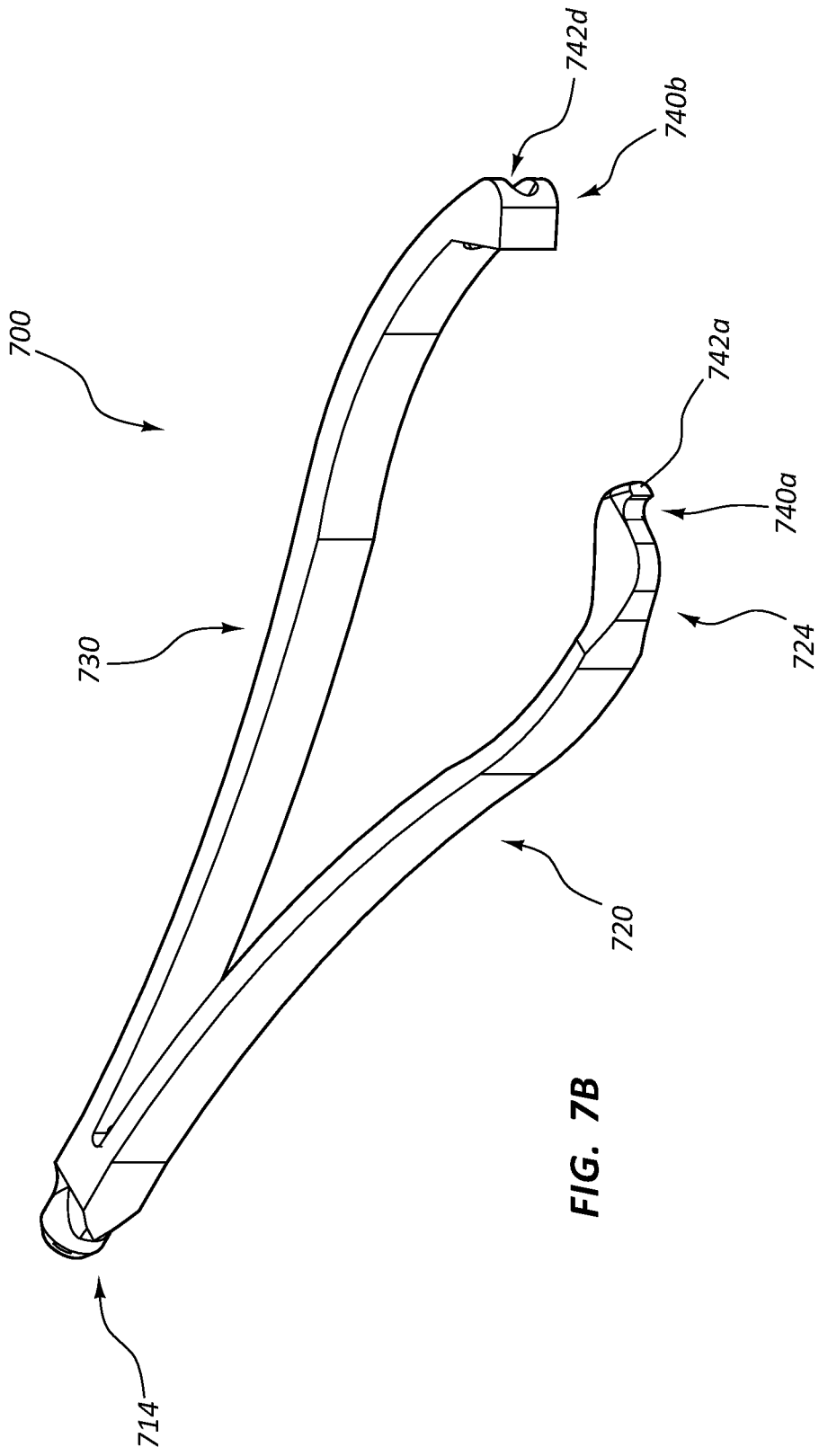
FIG. 7B is a second perspective view of the medical grasping device of FIG. 7A.

With continued reference to FIGS. 7A and 7B, each of the first resilient prong 720 and the second resilient prong 730 curves outwardly from an extension of a longitudinal axis 10 of the elongate member 710. In contrast, each of the protuberance 742a and the curved portions 742b, 742c curves inwardly toward the extension of the longitudinal axis 10 of the elongate member 610.

As depicted, each of the first resilient prong 720 and the second resilient prong 730 extends from the distal end 714 of the elongate member 710 such that the first resilient prong 720 extends in a substantially opposite direction from the second resilient prong 730. Stated another way, the extension of the first resilient prong 720 from the elongate member 710 generates or forms a substantially mirror image of the extension of the second resilient prong 730 from the elongate member 710, and vice versa. As illustrated, the first resilient prong 720 extends from a first portion at the distal end 714 of the elongate member 710 and the second resilient prong 730 extends from a second portion at the distal end 714 of the elongate member 710, wherein the first portion and the second portion are disposed at substantially opposite positions along a circumference of the distal end 714 of the elongate member 710. As such, each of the first resilient prong 720 and the second resilient prong 730 is substantially disposed within a single plane. Other dispositions of the first and second resilient prongs 720, 730 around the circumference of the distal end 714 of the elongate member are also within the scope of this disclosure.

Figure 7D:
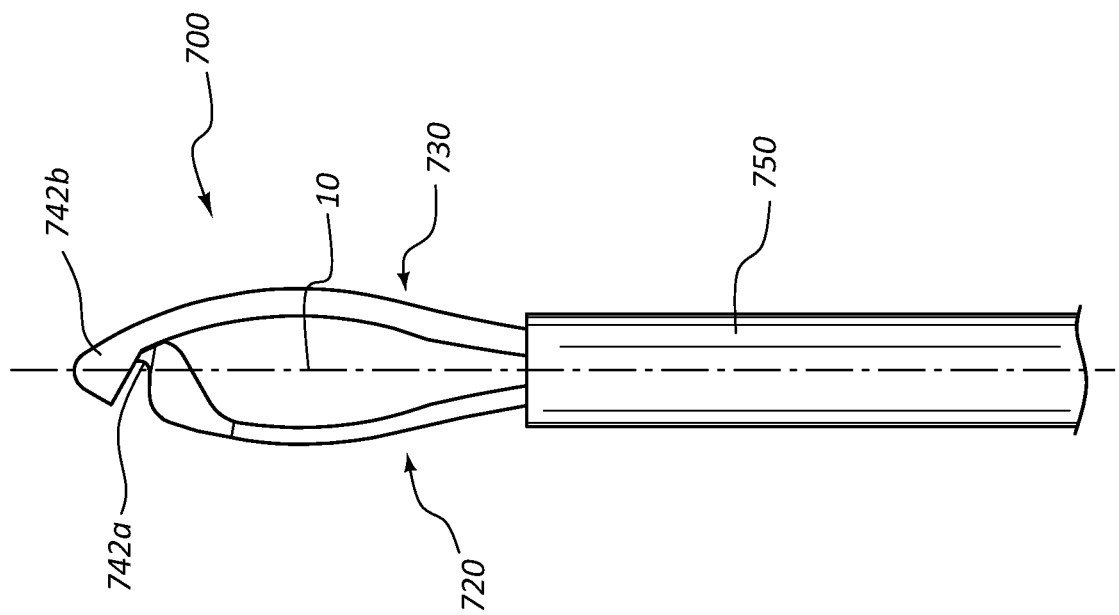
FIG. 7D is a front view of the medical grasping device of FIG. 7A in a closed configuration.
Figure 7C:
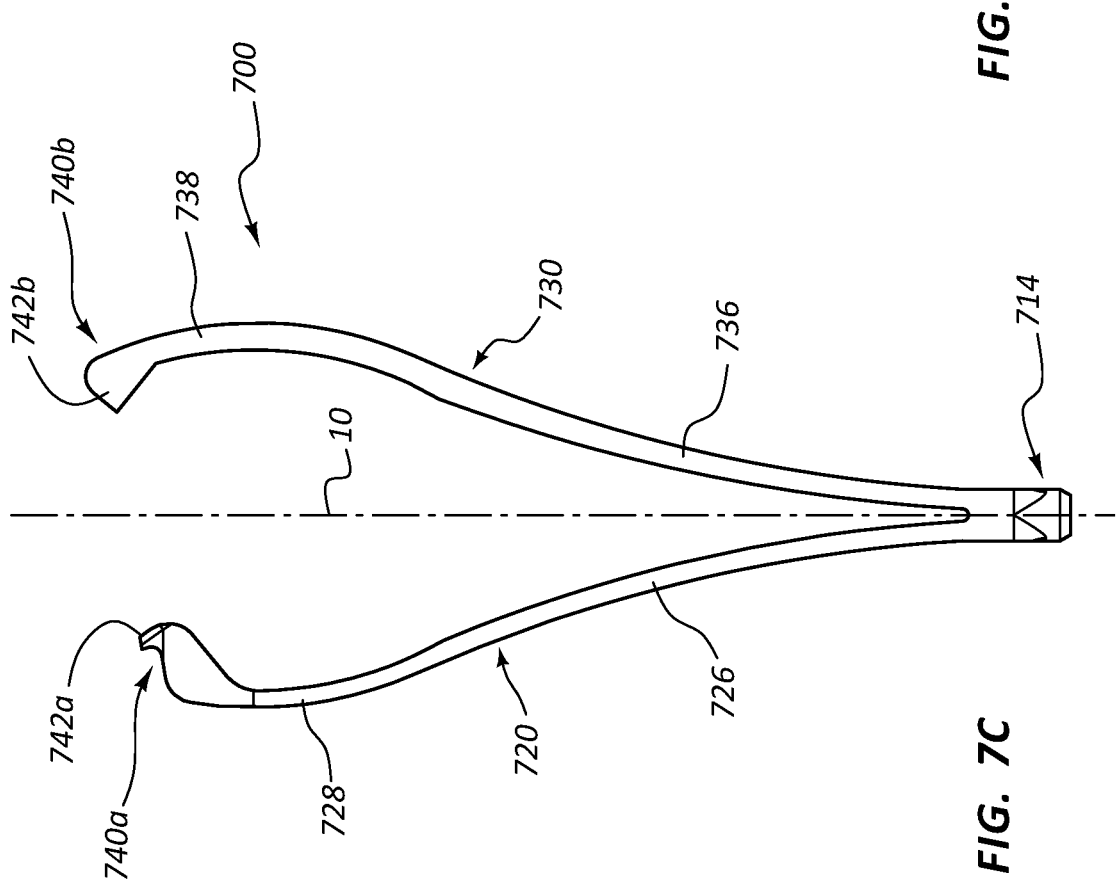
FIG. 7C is a front view of the medical grasping device of FIG. 7A in an open configuration.

FIG. 7C is a front view of a portion of the medical grasping device 700 of FIG. 7A in an open configuration. As depicted, the first resilient prong 720 comprises a concave proximal portion 726 and a convex distal portion 728. Likewise, the second resilient prong 730 comprises a concave proximal portion 736 and a convex distal portion 738. The concave proximal portions 726, 736 are concave with respect to the extension of the longitudinal axis 10 of the elongate member 710, and the concave proximal portions 726, 736 are positioned between the elongate member 710 and the convex distal portions 728, 738, respectively. The convex distal portions 728, 738 are convex with respect to the extension of the longitudinal axis 10 of the elongate member 710, and the convex distal portions 728, 738 extend from distal ends of the concave proximal portions 726, 736, respectively.

In some embodiments, the first resilient prong 720 and/or the second resilient prong 730 may comprise a first curve centered on a point outside of the first curve and a second curve centered on a point inside of the second curve. The radius of the first curve may be different from the radius of the second curve. Additionally, the first curve and the second curve may comprise a constant and/or a changing radius of curvature. In various embodiments, the first resilient prong 720 and/or the second resilient prong 730 may comprise an inflection point where the first resilient prong 720 and/or the second resilient prong 730 changes concavity.

As depicted in FIG. 7C, the first resilient prong 720 may have a shorter length as compared to the second resilient prong 730 and may also have greater flexibility or resilience (i.e., the first resilient prong 720 may experience greater flexion than the second resilient prong 730 in response to an equally applied force on the sides of the medical grasping device 700) to drive the protuberance 742a upwardly into the window 742d of the second resilient prong 730 when the medical grasping device 700 is in the closed configuration. In some embodiments, both the first and second resilient prongs 720, 730 may be made from the same material, such as NITINOL, but the first resilient prong 720 may have a reduced thickness as compared to the second resilient prong 730 to increase the flexibility of the first resilient prong 720. For example, in some embodiments, the thickness of the first resilient prong 720 may be between 30-60% less than the thickness of the second resilient prong 730. In other embodiments, only the convex distal portion 728 adjacent the first engagement feature 740a may have a reduced or tapered thickness to increase the flexibility of the distal portion 728, while the remaining portions of the first resilient prong 720 may have a substantially similar thickness as the second resilient prong 720.

In yet other embodiments, the first and second resilient prongs 720, 730 may have equal thicknesses, but the first resilient prong 720 may be made from a different, more flexible material than the second resilient prong 730. Additional details of the interlocking mechanism of the medical grasping device 700 are provided below with particular reference to FIG. 7D.

FIG. 7D is a front view of a portion of the medical grasping device 700 of FIG. 7A in a closed configuration. The following description provides additional details relating to the bending action of the first and second resilient prongs 720, 730 as the medical grasping device 700 is urged toward the interlocked and closed configuration by the delivery sheath 750. With collective reference to FIGS. 7C and 7D, as the first and second resilient prongs 720, 730 are retracted into the delivery sheath 750, the prongs 720, 730 are urged to move toward the longitudinal axis 10, thereby drawing the protuberance 742a and the curved portions 742b, 742c toward one another. Because of the greater flexibility of the first resilient prong 720, the protuberance 742a is drawn toward the longitudinal axis 10 more quickly than the second resilient prong 730. In other words, distal displacement of the delivery sheath 750 a certain distance may cause the first resilient prong 720 to be drawn closer to the longitudinal axis than is the second resilient prong 730. Thus, as the resilient prongs 720, 730 are drawn together, the first resilient prong 720 may be displaced across a greater distance than the second resilient prong 730 as the resilient prongs 720, 730 transition from an open configuration to a closed configuration.

As the prongs 720, 730 are moved closer to the one another, the curvature and greater flexibility of the first resilient prong 720 urge the protuberance 742a to drop underneath the curved portions 742b, 742c and slide into the window 742d on the second resilient prong 730. As the medical grasping device 700 is further retracted into the delivery sheath 750, the first resilient prong 720 gradually straightens and slightly rotates the protuberance 742a in a counterclockwise direction, thereby driving the protuberance 742a further into the window 742d to securely interlock the first and second resilient prongs 720, 730 as the medical grasping device 700 is drawn further into the delivery sheath 750.

Again, as discussed above, in some embodiments, components of the medical grasping device 700 may be integrally formed. For example, the elongate member 710 and the first and second resilient prongs 720, 730 may be integrally formed. In some other embodiments, components of the medical grasping device 700 may be discretely formed. For example, the elongate member 710 and the first and second resilient prongs 720, 730 may be discretely formed and subsequently coupled to each other.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially straight" is recited with respect to a feature, it is understood that in further embodiments, the feature can have a precisely straight configuration.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. A medical grasping device for use in an interventional procedure in a body lumen of a patient, the medical grasping device comprising:
an elongate member;
a first resilient prong extending from a distal end of the elongate member, the first resilient prong comprising a first engagement feature, wherein the first engagement feature includes a first retaining face oriented at a first angle relative to an extension of a longitudinal axis of the elongate member when the medical grasping device is in an open configuration; and
a second resilient prong extending from a distal end of the elongate member, the second resilient prong comprising a second engagement feature, wherein the second engagement feature includes a second retaining face oriented at a second angle relative to the longitudinal axis of the elongate member when the medical grasping device is in the open configuration;
wherein the first retaining face is oriented at a third angle relative to the longitudinal axis of the elongate member and the second retaining face is oriented at a fourth angle relative to the longitudinal axis of the elongate member when the medical grasping device is in a closed configuration;
wherein the first and second angles are obtuse angles as measured from the longitudinal axis, taken from a side of the longitudinal axis opposite the first retaining face to a line extending from the first retaining face which intersects and extends beyond the longitudinal axis; and
wherein the third and fourth angles are acute angles as measured from the longitudinal axis, taken from a side of the longitudinal axis opposite the second retaining face to a line extending from the second retaining face which intersects and extends beyond the longitudinal axis.

2. The medical grasping device of claim 1, wherein the first and second engagement features are configured to interlock to secure a medical device when the medical grasping device is in the closed configuration.

3. The medical grasping device of claim 1, wherein the first and second engagement features are configured to interlock to secure a medical device when the medical grasping device is driven from the open configuration to the closed configuration, wherein the first and second angles each change incrementally to the third angle and the fourth angle, respectively, as the medical grasping device is driven from the open configuration to the closed configuration.

4. The medical grasping device of claim 1, wherein the first engagement feature of the first resilient prong comprises a curved portion disposed at a distal end of the first resilient prong, and wherein the second engagement feature of the second resilient prong comprises two curved portions separated by a slot therebetween, the two curved portion disposed at a distal end of the second resilient prong, wherein the curved portion of the first resilient prong is configured to interlock with the two curved portions of the second resilient prong when the distal ends of the first and second resilient prongs are displaced toward each other, and wherein the curved portion of the first resilient prong is positioned in the slot between the two curved portions of the second resilient prong when the first and second prongs are interlocked.

5. The medical grasping device of claim 1, wherein each of the first resilient prong and the second resilient prong comprises a concave proximal portion and a convex distal portion, wherein the concave proximal portion is concave with respect to the extension of the longitudinal axis of the elongate member, wherein the concave proximal portion is positioned between the elongate member and the convex distal portion, wherein the convex distal portion is convex with respect to the extension of the longitudinal axis of the elongate member and wherein the convex distal portion extends from a distal end of the concave proximal portion.

6. The medical grasping device of claim 1, wherein the first and second resilient prongs are each formed of a shape memory alloy.

7. The medical grasping device of claim 1, further comprising:
a delivery sheath disposed around at least a portion of the medical device such that the medical device is longitudinally displaceable within the delivery sheath, wherein upon proximal displacement of the first and second resilient prongs into a lumen of the delivery sheath the first and second engagement features are displaced toward each other, and wherein upon distal displacement of the first and second resilient prongs out of the lumen of the delivery sheath the first and second engagement features are displaced away from each other.

8. The medical device of claim 1, further comprising a third resilient prong extending from a distal end of the elongate member.

9. A medical grasping device for use in an interventional procedure in a body lumen of a patient, the medical grasping device comprising:
an elongate member;
a first resilient prong extending from a distal end of the elongate member, the first resilient prong comprising a first engagement feature formed at a distal end of the first resilient prong; and
a second resilient prong extending from a distal end of the elongate member, the second resilient prong comprising a second engagement feature formed at a distal end of the second resilient prong, wherein a length of the first resilient prong is shorter than a length of the second resilient prong;
wherein the first engagement feature includes a protuberance extending outwardly from the distal end of the first resilient prong and wherein the second engagement feature includes a slot sized to receive the protuberance such that the protuberance is seated against the slot when the first and second resilient prongs are engaged.

10. The medical grasping device of claim 9, wherein the first engagement feature of the first resilient prong comprises a curved portion disposed at a distal end of the first resilient prong, and wherein the second engagement feature of the second resilient prong comprises at least one curved portion, the at least one curved portion disposed at a distal end of the second resilient prong.

11. The medical grasping device of claim 10, wherein each of the first resilient prong and the second resilient prong curves outwardly from an extension of a longitudinal axis of the elongate member, and wherein each of the curved portions curves inwardly toward the extension of the longitudinal axis of the elongate member.

12. The medical grasping device of claim 9, wherein displacing the first and second resilient prongs toward each other drives the protuberance into the slot of the second engagement feature.

13. The medical grasping device of claim 9, wherein the first resilient prong includes a distal portion adjacent the distal end of the first resilient prong, the distal portion having a smaller thickness as compared to a thickness of a distal portion of the second resilient prong, such that the convex distal portion of the first resilient prong experiences greater flexibility than the convex distal portion of the second resilient prong when the first and second resilient prongs are displaced toward each other.

14. The medical grasping device of claim 9, wherein the first resilient prong experiences greater flexibility than the second resilient prong when the first and second resilient prongs are displaced toward each other.

15. A method of retrieving a foreign object from a body lumen, comprising:
disposing the grasping device of claim 1 to a position within a body lumen adjacent a target foreign object;
actuating the grasping device such that the first and second engagement features interlock with each other to secure the engaged target foreign object; and
longitudinally displacing the grasping device to dislodge the secured target foreign object from a position within the body lumen.

16. A method of retrieving a foreign object from a body lumen, comprising:
disposing the grasping device of claim 9 to a position within a body lumen adjacent a target foreign object;
actuating the grasping device such that the first and second engagement features interlock with each other to secure the engaged target foreign object; and
longitudinally displacing the grasping device to dislodge the secured target foreign object from a position within the body lumen.

* * * * *

UNITED STATES PATENT AND TRADEMARK OFFICE
CERTIFICATE OF CORRECTION

PATENT NO. : 10,863,998 B2
APPLICATION NO. : 15/608359
DATED : December 15, 2020
INVENTOR(S) : Mottola et al.

Page 1 of 1

It is certified that error appears in the above-identified patent and that said Letters Patent is hereby corrected as shown below:

In the Claims

Column 23, Line 21 reads, ". . . the two curved portion . . ." which should read, ". . . the two curved portions . . ."

Signed and Sealed this
Second Day of March, 2021

Drew Hirshfeld
*Performing the Functions and Duties of the*
*Under Secretary of Commerce for Intellectual Property and*
*Director of the United States Patent and Trademark Office*